United States Patent [19]
McElroy et al.

[11] Patent Number: 5,641,876
[45] Date of Patent: Jun. 24, 1997

[54] RICE ACTIN GENE AND PROMOTER

[75] Inventors: David McElroy, Canberra, Australia; Ray Wu, Ithaca, N.Y.

[73] Assignee: Cornell Research Foundation, Inc., Ithaca, N.Y.

[21] Appl. No.: 144,602

[22] Filed: Oct. 27, 1993

Related U.S. Application Data

[63] Continuation-in-part of Ser. No. 762,680, Sep. 18, 1991, abandoned, and a continuation of Ser. No. 461,490, Jan. 5, 1990, abandoned.

[51] Int. Cl.$^6$ .................................................. C12N 15/11
[52] U.S. Cl. .......................................... 536/24.1; 435/320.1
[58] Field of Search ....................... 536/24.1; 435/172.3, 435/320.1

[56] References Cited

PUBLICATIONS

Nairn et al (1988) Gene vol. 65: 247–257.
Oard et al. (1989) Plant Cell Reports vol. 8: 156–160.
Callis et al. (1987) Genes and Development vol 1: 1183–1200.
Frederickson et al (1989) Nucleic Acids Research vol. 17 (1): 253–270.
Wang, Y., et al., Molecular and Cellular Biology 12(8):3399–3406 (1992).
Reece, K.S., et al., Plant Molecular Biology 14:621–624 (1990).
Gonzalez–y–Merchand, J.A., and Cox, R.A., J Mol Biol 202:161–168 (1988).
Brinster, R.L., et al., Proc Natl Acad Sci USA 85:836–840 (1988).
McElroy, D., et al., Plant Molecular Biology 15:257–268 (1990).
Vandekerckhove, J. and Weber, K., Nature 276:720–721 (1978).
McElroy, D. et al., Plant Molecular Biology 14:163–171 (1990).
McElroy, D. et al., The Plant Cell 2:163–171 (1990).
McElroy, D. et al., Mol Gen Genet 231:150–160 (1991).
Nagao, R.T. et al., DNA 2(1):1–9 (1981).
Ng, SY et al., Nucleic Acids Research 17(2):601–615 (1989).
Shah, D.M. et al., Journal of Molecular and Applied Genetics 2:111–126 (1983).
Staiger, C.J. et al., Protoplasma 141:1–12 (1987).
Zhang, W. et al., The Plant Cell 3:1155–1165 (1991).
McElroy, D. et al., J Cellular Biochem, Supplement 15A:75, abstract no. A 335 (1991).

*Primary Examiner*—Che S. Chereskin
*Attorney, Agent, or Firm*—Nixon, Hargrave, Devans & Doyle

[57] ABSTRACT

The present invention describes the genomic nucleotide sequence of, and isolation of a strong intron-dependent promoter for, rice actin genes.

4 Claims, 4 Drawing Sheets pRAc15'.21VG pRAc15'.13XG pRAc15'.09RG pRAc15'.21VRʳG pRAc15'.09GIΔ8 pRAc15'.09RGIΔ1 pRAc15'.09RGIΔ12 pRAc15'.09RIDS⁻ pRAc15'.09RGI⁻ pRAc15'.21VrG pAl₁GusN

RICE ACTIN GENE AND PROMOTER

This application is a continuation-in-part of U.S. Ser. No. 07/762,680, filed Sep. 18, 1991, now abandoned, which was a continuation of U.S. Ser. No. 07/461,490, filed Jan. 5, 1990, now abandoned.

Significant progress has recently been made in the application of tissue culture and gene transfer techniques to previously recalcitrant monocotyledonous plants, such as rice. Rice protoplasts have been shown to transiently express a foreign gene after transformation by electroporation, and stable genomic integration of foreign DNA, following polyethylene-glycol-mediated transformation of rice cells, has been previously demonstrated.

One of the major limitations in rice transformation technology has been the lack of an efficient promoter for high level constitutive expression of foreign genes in transgenic plants. The cauliflower mosaic virus (CaMV) 35S promoter has been widely used for this purpose in a number of plant transformation systems, however, the CaMV 35S promoter has shown low activity in transforming rice cells, and recent reports suggest that the pattern of CaMV 35S promoter activity in transgenic plants may not be constitutive. Work in our laboratory suggests that the 5' region of the maize Adh1 gene containing the promoter, 5'-coding exon and 5'-intron, is 20 to 30 times more active than the CaMV 35S promoter for transient gene expression in transformed rice protoplasts and calli, however, the activity of AdH1 promoter in transformed rice protoplasts is maximally induced by anaerobic stress and its activity is not constitutive in all transformed rice tissues. As a result, a number of alternative promoter elements for rice transformation are currently under investigation.

It is, therefore, the purpose of the present invention to describe an efficient promoter for rice transformation, and in doing so have based such a promoter upon a rice actin gene that displays a constitutive spatial and temporal pattern of transcript abundance.

Cytoplasmic actin is a fundamental and essential component of the eukaryotic cell and cytoskeleton. In higher-plant cells a number of cellular processes, such as cytoplasmic streaming, extension growth and cell division, are believed to involve cytoskeletal actin protein. Actin has been found to be encoded by gene families in all higher plants studied to date. A unique feature of these plant actin genes, in contrast to the situation for animal actin genes, has been their conservation of gene structure. All of the studied plant actin genes are reported to consist of four coding exons of conserved length, separated by three introns of variable length. In each of these cases the coding regions of the plant actin genes have been deduced following a comparison of their potential translations products with that of previously published animal actin protein sequences. However, in a number of animal actin genes there exists a 5' transcribed, but untranslated, sequence (5'-noncoding exon), separated by an intron (5'-intron from the exon containing the first translated codon (5'-coding exon). Although it has been suggested that a 5'-noncoding exon may exist in plant actin genes, such an exon would fail to be detected in any comparison of the coding region of plant and animal actin genes.

In rice, there are at least 8 actin-like sequences per haploid genome, of which four have been isolated and shown to differ from each other in the tissue and stage specific abundance of their respective transcripts. One rice actin gene, RAc1, was found to encode a transcript that is relatively abundant in all rice tissues, and at all developmental stages examined. In view of the high level constitutive abundance of the rice RAc1 transcript the present invention describes the isolation and partial sequencing of a genomic clone containing the rice RAc1 5' flanking and 5'-transcribed, non-translated, regions. From such clones, a number of RAc1-GUS fusions plasmids were constructed and used in transient expression assays of transformed rice protoplasts. The results from these assays suggest that the regulatory element(s) necessary for maximal RAc1 promoter activity in transformed rice protoplasts are located within a region 1.3 kb upstream of the RAc1 translation initiation codon. The RAc1 promoter is 5 times more active than the maize Adh1 promoter in transformed rice cells, suggesting that the RAc1 5' region contains an efficient promoter for rice transformation.

As a first step towards a characterization of the actin gene in rice, several clones from a rice genomic library representing four unique actin sequences were isolated. A rice (*Oryza sativa* var., cv. IR26) genomic library in lambda-EMBL4 was screened with a heterologous actin probe. Fourteen independent clones were isolated and subcloned into pUC13. By mapping restriction sites and carrying out cross-hybridization studies, four different classes of clones were identified and designated RAc1, RAc2, RAc3 and RAc7.

Sequencing of the subcloned actin genes was carried out by the dideoxynucleotide chain termination method and computer analysis of the resulting sequences was done. The nucleotide sequences of the coding regions of the four actin genes appear in the EMBL Gene Bank and DDB7 Nucleotide Sequence Databases under the accession numbers X15865 RAc1; X15864 RAc2; X15862 RAc3; and X15863 RAc7.

Prior to identifying those sequences which regulate RAc1 expression, its complete genomic structure was determined. By characterizing an RAc1 cDNA clone (EMBL data Bank accession number X16280) and 5' end mapping the RAc1 transcript, the structure of the RAc1 gene was determined and the position of a 5'-noncoding exon in its genomic sequence was identified and located. This represents the first complete structural characterization of plant actin gene and is one of few reported cases of a 5'-noncoding exon in a plant gene.

A complete understanding of all aspects of the present invention can be better understood from reference to the accompanying figures (and examples) in which.

Figure 1A:
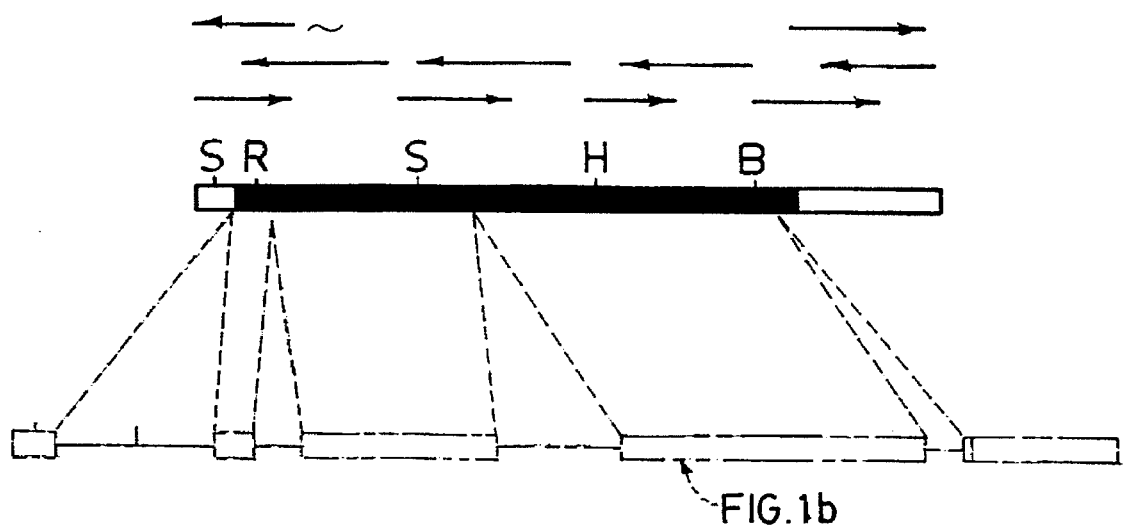
FIG. 1a is a restriction map of the pcRAc1.3 cDNA insert, according to the present invention.

The identification of the complete genomic structure was accomplished utilizing the protocols described in the following examples:

EXAMPLE 1

(A) Screening the lambda-gt11 cDNA library:

A rice (*Oryza sativa* IR36) lambda-gt11 cDNA library was prepared from six-day-old etiolated leaf tissue. Primary and secondary screenings for rice actin cDNA clones were carried out by hybridization with a 260 bp, $^{32}$P-dATP labeled BamH1-HindIII restriction fragment from the rice actin genomic clone pRAc2. Tertiary screening was carried out using rice actin gene-specific probes. RAc1-like cDNA clones were identified using a 900-bp BamH1-HindIII restriction fragment probe from the 3' untranslated end of the rice actin genomic clone pRAc1.

(B) Restriction mapping and nucleotide sequencing:

Actin positive clones from tertiary screening of the lambda-gt11 cDNA library were further characterized by restriction mapping. Restriction fragments from the cDNA insert of the RAc1 positive clone pcRAc1.3 were subcloned into pBS-KS vectors for nucleotide sequencing. Double-stranded DNA sequencing using $^{35}$S-dATP was carried out using a T7 polymerase sequencing kit following the manufacturer's (Pharmacia) modification of the Sanger et al dideoxynucleotide sequencing procedure. The 5' and 3' ends of the pcRAc1.3 cDNA insert were further sequenced using two synthetic oligonucleotides; 5'-AAGCGGCCTCTACTACGC-3' and SEQ ID NO:1 5'-GAAGCATTTCCTGTGCACAAT-3' respectively and subsequently the sequence data were analyzed.

(C) 5'-end mapping of RAc1 transcript by Northern blot analysis and primer extension:

RNA isolation from seven-day-old rice shoots and Northern blotting were performed. 10 μg of total RNA samples were used in formaldehyde agarose gel electrophoresis and Northern analysis was carried out under stringent hybridization conditions (50% formamide, 50° C.). Restriction fragment probes for Northern hybridization were isolated from the 5'-untranslated end of the rice actin genomic clone pRAc1 and subcloned into pBS-KS vectors.

The primer extension analysis was performed using 1 μg of a synthetic oligonucleotide primer SEQ ID NO:3: 5'-CTTCTACCGGCGGCGGC-3' which was annealed to 25 μg of total RNA from seven-day-old rice shoots.

The cDNA library made with mRNA from six-day-old etiolated rice shoots according to Example 1 provided the cDNA clones corresponding to the multiple members of the rice actin gene family. Primary and secondary screening were conducted with a 260 bp Bam H1-Hind III restriction fragment—a fragment previously known to cross-hybridize with many members of the rice actin gene family—from the rice actin gene RAc2. Thirty four clones were identified which strongly hybridized to the non-specific RAc2 actin probe.

Tertiary screening of the 34 actin-positive clones was carried out using probes previously determined to be actin gene specific. Seven RAc1-like cDNA clones were identified which hybridized specifically to a 900 bp BamH1-HindIII restriction fragment from pRAc1. The nature of these clones was confirmed by restriction mapping and Southern blotting. The EcoRI insert from the lambda-gt 11 clone lambda-RAc1.3 was subcloned into a pBS-KS vector to produce the plasmid pcRAc1.3.

Using similar procedures, nine RAc3-like cDNA clones and eight RAc7-like cDNA clones were identified. No cDNA clones were identified which cross-hybridized with a RAc2 gene specific probe. The remaining ten actin-positive clones failed to cross-hybridize with any of the previously characterized actin gene-specific probes. These were classified into five groups on the basis of restriction mapping and cross-hybridization analysis. The isolation of cDNA clones representing eight distinct actin transcripts confirms that the actin gene family in rice is composed of at least eight unique members.

The insert from pcRAc1.3 was further subcloned into pBS-KS plasmids. Double stranded DNA was prepared for sequencing. The restriction enzyme map of the pcRAc1 insert and the sequencing strategy for determining its bases are summarized in FIG. 1a.

Figure 1B:
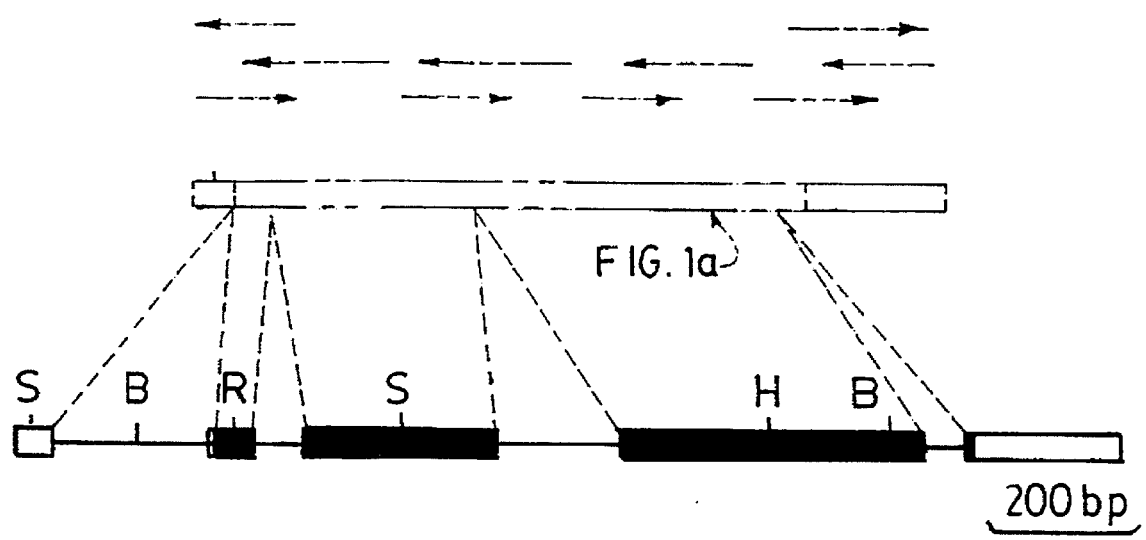
FIG. 1b is a restriction map and proposed structure of the RAc1 genomic clone according the the present invention.

More specifically, FIG. 1 describes the determination of the RAc1 gene structure by alignment of the pcRAc1.3 cDNA insert with the pRAc1 genomic clone. FIG. 1a shows the restriction map of the pcRAc1 cDNA insert with the strategy used to determine its base sequence. The horizontal arrows indicate the direction of sequencing and their length indicate the actual size of the sequence obtained. Horizontal arrows preceded with a siusoidal wave indicate the use of synthetic oligonucleotide primers. FIG. 1b shows the restriction map and proposed structure of the RAc1 genomic clone. Horizontal lines represent introns and boxes represent exons. Open boxes represent the transcribed but untranslated regions of exons, closed boxes represent the translated regions of exons. Restrictions sites: B, BamHI; H, HindIII; R, EcoRV; S, SstI. Dashed lines between the cDNA and genomic DNA restriction maps indicate the alignment of their homologous exons.

The tabulated sequence which depicts the nucleotide sequence of the rice actin gene RAc1, is depicted in the following sequence of 5643 nucleotides having SEQ ID NO:4:

| | | | | |
|---|---|---|---|---|
| GATATCCCTC | AGCCGCCTTT | CACTATCTTT | TTTGCCCGAG | TCATTGTCAT | 50 |
| GTGAACCTTG | GCATGTATAA | TCGGTGAATT | GCGTCGATTT | TCCTCTTATA | 100 |
| GGTGGGCCAA | TGAATCCGTG | TGATCGCGTC | TGATTGGCTA | GAGATATGTT | 150 |
| TCTTCCTTGT | TGGATGTATT | TTCATACATA | ATCATATGCA | TACAAATATT | 200 |
| TCATTACACT | TTATTAGAGG | TGGTCAGTAA | TAAACCCTAT | CACTATGTCT | 250 |
| GGTGTTTCAT | TTTATTTGCT | TTTAAACGAA | ATTGACTTCT | GATTCAATAT | 300 |
| TTAAGGATCG | CAATCGGCGT | GCAGTACTAA | TTCTGGTTGA | CGGAACTATA | 350 |
| CGTAAACTAT | TCAGCTTCAC | TCTATTAGGC | ACTACTTGAC | ACACCGGAGT | 400 |
| ACGTACGAAT | ACTCTATCAA | TTAGTCTCAG | TCTAACTTGT | TGAGACATGT | 450 |
| ACTATAGATT | ACTATTGTAC | CTTGACTCAC | TGTATGTATC | ACGTCTAATT | 500 |
| GAACTACACA | TATATACGCG | ATATTTTTTA | ATAACATTAA | AACCTACCTC | 550 |
| TATGTCAACA | ATGGTGTACG | ATAACCACAA | GTTTAGGAGG | TAAAAAAACA | 600 |
| TTGCCTTACG | CTGAAGTTAC | GCCTTAAAAA | TAAAGAGTAA | ATTTTACTTT | 650 |
| GACCACCCTT | CAATGTTCAC | TTTAGACCGG | TGGAACGCTC | CAGCCGTAAT | 700 |
| AGGATTCTGC | ACCTCACATG | CCTTAGCCGG | ATTATATTGC | CTGCCCACTT | 750 |
| TCTCACTCAT | ATCTGCAAGA | ATGTCTACTC | GCTAGAATTA | TCGCGATAGT | 800 |
| AGCTAGCATA | CTCGAGGTCA | TTCATATGCT | TGAGAAGAGA | GTCGGGATAG | 850 |
| TCCAAAATAA | AACAAAGGTA | AGATTACCTG | GTCAAAAGTG | AAAACATCAG | 900 |
| TTAAAAGGTG | GTATAAGTAA | AATATCGGTA | ATAAAAGGTG | GCCCAAAGTG | 950 |
| AAATTTACTC | TTTTCTACTA | TTATAAAAAT | TGAGGATGTT | TTGTCGGTAC | 1000 |
| TTTGATACGT | CATTTTTGTA | TGAATTGGTT | TTTAAGTTTA | TTCGCGATTT | 1050 |
| TGGAAATGCA | TATCTGTATT | TGAGTCGGGT | TTTAAGTTCG | TTTGCTTTTG | 1100 |

| | | | | | |
|---|---|---|---|---|---|
| TAAATACAGA | GGGATTTGTA | TAAGAAATAT | CTTTAAAAAA | ACCCATATGC | 1150 |
| TAATTTGACA | TAATTTTTGA | GAAAAATATA | TATTCAGGCG | AATTCTCACA | 1200 |
| ATGAACAATA | ATAAGATTAA | AATAGCTTGC | CCCCGTTGCA | GCGATGGGTA | 1250 |
| TTTTTCTAG | TAAAATAAAA | GATAAACTTA | GTCTCAAAAC | ATTTACAAAA | 1300 |
| ACAACCCCTA | AAGTCCTAAA | GCCCAAAGTG | CTATGCACGA | TCCATAGCAA | 1350 |
| GCCCAGCCCA | ACCCAACCCA | ACCCAACCCA | CCCCAGTGCA | GCCAACTGGC | 1400 |
| AAATAGTCTC | CACACCCCGG | CACTATCACC | GTGAGTTGTC | CGCACCACCG | 1450 |
| CACGTCTCGC | AGCCAAAAAA | AAAAAAAGAA | AGAAAAAAAA | GAAAAAGAAA | 1500 |
| AAACAGCAGG | TGGGTCCGGG | TCGTGGGGGC | CGGAAAAGCG | AGGAGGATCG | 1550 |
| CGAGCAGCGA | CGAGGCCGGC | CCTCCCTCCG | CTTCCAAAGA | AACGCCCCCC | 1600 |
| ATCGCCACTA | TATACATACC | CCCCCCTCTC | CTCCCATCCC | CCCAACCCTA | 1650 |
| CCACCACCAC | CACCACCACC | TCCTCCCCCC | TCGCTGCCGG | ACGACGAGCT | 1700 |
| CCTCCCCCCT | CCCCCTCCGC | CGCCGCCGGT | AACCACCCCG | CGTCCCTCTC | 1750 |
| CTCTTTCTTT | CTCCGTTTTT | TTTTTCCGTC | TCGTCTCGAT | CTTTGGCCTT | 1800 |
| GGTAGTTTGG | GGGCGAGAGG | CGGCTTCGTC | GCCCAGATCG | GTGCGCGGGA | 1850 |
| GGGGCGGGAT | CTCGCGGCTG | GGTCTCGGCG | TGCGGCCGGA | TCCTCGCGGG | 1900 |
| GAATGGGGCT | CTCGGATGTA | GATCTGATCC | GCCGTTGTTG | GGGGAGATGA | 1950 |
| TGGGGCGTTT | AAAATTTCGC | CATGCTAAAC | AAGATCAGGA | AGAGGGGAAA | 2000 |
| AGGGCACTAT | GGTTTATATT | TTTATATATT | TCTGCTGCTG | CTCGTCAGGC | 2050 |
| TTAGATGTGC | TAGATCTTTC | TTTCTTCTTT | TTGTGGGTAG | AATTTGAATC | 2100 |
| CCTCAGCATT | GTTCATCGGT | AGTTTTTCTT | TTCATGATTT | GTGACAAATG | 2150 |
| CAGCCTCGTG | CGGAGCTTTT | TTGTAGGTAG | AAGATGGTCA | ACGCCAGGGA | 2200 |
| TATCCAGCCC | CTCGTCTGCG | ATAATGGAAC | TGGTATGGTC | AAGGTAAGCT | 2250 |
| GTTTGGATCT | CAGGGTGGTT | TCCGTTACC | GAAATGCTGC | ATTTCTTGGT | 2300 |
| AGCAAAACTG | AGGTGGTTTG | TGTCAGGCTG | GGTTCGCCGG | AGATGATGCG | 2350 |
| CCCAGGGCTG | TCTTCCCCAG | CATTGTCGGC | CGCCCTCGCC | ACACCGGTGT | 2400 |
| CATGGTCGGA | ATGGGCCAGA | AGGACGCCTA | CGTCGGCGAC | GAGGCGCAGT | 2450 |
| CCAAGAGGGG | TATCTTGACC | CTCAAGTACC | CCATCGAGCA | TGGTATCGTC | 2500 |
| AGCAACTGGG | ATGATATGGA | GAAGATCTGG | CATCACACCT | TCTACAACGA | 2550 |
| GCTCCGTGTG | GCCCCGGAGG | AGCACCCCGT | CCTCCTCACC | GAGGCTCCTC | 2600 |
| TCAACCCCAA | GGCCAATCGT | GAGAAGATGA | CCAGATCAT | GTTTGAGACC | 2650 |
| TTCAACACCC | CTGCTATGTA | CGTCGCCATC | CAGGCCGTCC | TCTCTCTGTA | 2700 |
| TGCCAGTGGT | CGTACCCAAG | GTGAGCACAT | TCGACACTGA | ACTAAAGGC | 2750 |
| TGTGAGGATG | AATTTTAATT | TTGACATTCA | CATGTAGATG | AGATTTAGTT | 2800 |
| CTGCAATCTT | CAATTGTCAT | ACAGCAAGAC | TATATAATAG | CTTTCAAAAT | 2850 |
| AAAATCATAG | GCAGTTCTCA | TAAATGGAAT | CATGTTTGAA | CATCCTAATT | 2900 |
| CTGTTGGCAT | GGAGTGCTTT | GACATTTTGA | AGTGTGCATC | AGTGTGAATA | 2950 |
| ACTGAATTTC | CTTTTCCCAA | GGTATTGTGT | TGGACTCTGG | TGATGGTGTC | 3000 |
| AGCCACACTG | TCCCCATCTA | TGAAGGATAT | GCTCTCCCCC | ATGCTATCCT | 3050 |
| TCGTCTCGAC | CTTGCTGGGC | GTGATCTCAC | TGATTACCTC | ATGAAGATCC | 3100 |
| TGACGGAGCG | TGGTTACTCA | TTCACCACAA | CGGCCGAGCG | GGAAATTGTG | 3150 |
| AGGGACATGA | AGGAGAAGCT | TTCCTACATC | GCCCTGGACT | ATGACCAGGA | 3200 |
| AATGGAGACT | GCCAAGACCA | GCTCCTCCGT | GGAGAAGAGC | TACGAGCTTC | 3250 |
| CTGATGGACA | GGTTATCACC | ATTGGTGCTG | AGCGTTTCCG | CTGCCCTGAG | 3300 |
| GTCCTCTTCC | AGCCTTCCTT | CATAGGAATG | GAAGCTGCGG | GTATCCATGA | 3350 |
| GACTACATAC | AACTCCATCA | TGAAGTGCGA | CGTGGATATT | AGGAAGGATC | 3400 |
| TATATGGCAA | CATCGTTCTC | AGTGGTGGTA | CCACTATGTT | CCCTGGCATT | 3450 |
| GCTGCAGGA | TGAGCAAGGA | AGATCACTGC | CTTGCTCCTA | GCAGCATGAA | 3500 |
| GATCAAGGTG | GTCGCCCCTC | CTGAAAGGAA | GTACAGTGTC | TGGATTGGAG | 3550 |
| GATCCATCTT | GGCATCTCTC | AGCACATTCC | AGCAGGTAAA | TATACAAATG | 3600 |
| CAGCAATGTA | GTGTTGTTTA | CCTCATGAAC | TTGATCAATT | TGCTTACAAT | 3650 |
| GTTGCTTGCC | GTTGCAGATG | TGGATTGCCA | AGGCTGAGTA | CGACGAGTCT | 3700 |
| GGCCCATCCA | TTGTGCACAG | GAAATGCTTC | TAATTCTTCG | GACCCAAGAA | 3750 |
| TGCTAAGCCA | AGAGGAGCTG | TTATCGCCGT | CCTCCTGCTT | GTTTCTCTCT | 3800 |
| TTTTGTTGCT | GTTTCTTCAT | TAGCGTGGAC | AAAGTTTTCA | ACCGGCCTAT | 3850 |
| CTGTTATCAT | TTTCTTCTAT | TCAAAGACTG | TAATACCTAT | TGCTACCTGT | 3900 |
| GGTTCTCACT | TGTGATTTTG | GACACATATG | TTCGGTTTAT | TCAAATTTAA | 3950 |
| TCAGATGCCT | GATGAGGGTA | CCAGAAAAAA | TACGTGTTCT | GGTTGTTTTT | 4000 |
| GAGTTGCGAT | TATTCTATGA | AATGAATAAC | ATCGAAGTTA | TCATCCCAGT | 4050 |
| ATTTTCGCAT | GAATGTTCTT | TTCTTCTGTC | TTGTGCATCA | GTGATCTAGT | 4100 |
| GCATGGGAGT | TTGTATTGTG | ATGTTCGACA | TCACGTAACT | TCCACTTTGC | 4150 |
| CTTTGCTGTT | CGATATTTTA | ATGACATGTC | ACACACACTT | CTGCTACTTT | 4200 |
| TCTTTCTTGG | CTATTGTGCC | AGCATGATGC | AAGATGCATC | ACACGATCAG | 4250 |
| ATATATTCTC | ATCGTCAGGC | TTTCAGGCAC | AGAGCACGCT | TTGCGCTTAA | 4300 |
| AAGTTGTACC | GCCAGTAGAC | ATCCCCTGTA | GAAGTGATAA | TCTTTTCACT | 4350 |
| TTTCTTAAAG | AAATTGAGAG | GGGAAATGGA | ACCATGTGGA | TCAGAGAAGC | 4400 |
| TTTTGTTTCT | TACACAAGAA | TATTTGGTAC | AGTGGGGGTC | CTATGTTCGT | 4450 |
| GGGTTCGTGG | CTTGGCTCCC | TGTCTTCAAC | CAAGTGTTTT | CAGTTCAACA | 4500 |
| TGTTAGCGTG | TAGAAAGAGC | ACAATTCTGT | TTATCTCCAA | GGTAAAATGT | 4550 |
| GGCATTCTGT | TAAAGAACAT | GATCCTGCCA | ATTTTTTAAG | TTTCAATGGA | 4600 |
| AGAGGAATGT | AAAGCTTTCT | ATGGTTTGTG | TACACAACAC | AGTGGAAGAG | 4650 |
| GAGTGCAAGC | TTTCTATGGT | TTGTGTGCGC | GTTGTGGTGC | AGCACTTCAA | 4700 |
| TTTTGTTAGA | AATGAAAGAA | AAAAAAGGAT | GATCATGCTT | ATAGTAAATC | 4750 |
| ACTCTTTTTC | CTCGCCTTCT | GTACGTTTTG | ACTTGACAAG | ATTTTAAAAT | 4800 |
| CTGTACATGA | CCTTTGTTTT | AAAATTACTT | TATGTATTTC | CATCTTTCAA | 4850 |
| GTTATGCAGA | TGTCATCACA | AATTGTTACA | CCAATCACCA | GGCTGGCTGT | 4900 |
| TTATATATTA | TCAGACCAGG | CTATATAGAG | TATACTATAC | TAACTGTTCA | 4950 |
| TATTATCTGG | AAATCTTGCT | TGCTACTTGA | GCGGGAAAAG | GGTATAGATA | 5000 |
| TGAGGTTAAG | GAACGAAGCG | GCAGCAAATC | GAGGCTCTCT | CTGAAATCAT | 5050 |
| TTTACATCTA | CAAAAGCACA | TTTAACCTTT | TCTAGAACAC | ATATGTTACT | 5100 |

-continued

| | | | | |
|---|---|---|---|---|
| TAGAAGCAGG | AAGTTCATGC | AAAATTTCAT | CGACAAGATA | ACCAGGGCGG 5150 |
| CACTGGAAGA | GTTATCTTTT | ACCTCAATCT | GTATACACTC | AAAGTTACTC 5200 |
| GGATTGTACA | TTGGCTAAAA | GTTTCCCTGT | TTCATTTGAA | CCACCTCAGC 5250 |
| AAAAGCAACC | TGAAGAGTTT | GTTGTGCAAA | GGTAAAAACC | TTCCCCCAGA 5300 |
| CTTTGATCCT | TCCCTTGCAT | ATCTAAGGGC | ATCACGGTGA | GGTCACTGTA 5350 |
| CCGCAAGCAT | TAGTCCAACA | CAAAGCCATT | CTTTGCTTCT | TTTGTCCACC 5400 |
| GTTTCAATAT | GTATACATCT | GGTATGGTGC | GTACATCAAG | GGCCAAGAAT 5450 |
| ACTCTTAGTA | TATGCCGGCA | CAAGCTACCA | CAACTCTCAA | ACTTGCAGCA 5500 |
| GCTGCACTTA | GCTATATTGC | CAGAAGTATC | ATACCTGACT | CTGCATGTGG 5550 |
| CTTCAGTATG | GTCCTTTGTG | ACACTATACA | CAGCAATCAA | CCCATCATTG 5600 |
| TCAAGACTAG | AGATATATAA | TAGCCTAAAG | ATCCAATGAA | TCC 5643 |

An alignment between the sequence of the RAc1 cDNA clone and that of the RAc1 genomic sequence was used to determine the structure of the RAc1 gene shown above. Translation of the pcRAc1.3 insert in all three reading frames identified a potential coding region of 1131 nucleotides. The potential coding region of the RAc1 cDNA, if translated in vivo, would code for 377 amino acids and an actin protein of 41.9 kDA estimated molecular mass.

This analysis identified three introns, interrupting the gene at the same places in the RAc1 coding sequence as those previously reported for all other plant actins. The analysis also identified an additional intron within the transcribed sequence of RAc1 which is 5' of the region containing the translation initiation codon. This 5'-intron separated a 79 bp GC-rich 5'-noncoding exon from an exon coding the translation initiation codon.

In the sequence depicted above, the promoter according to the present invention lies within nucleotides 4 to 2202 of SEQ ID NO:4, more particularly, the promoter has a nucleotide sequence as shown in nucleotides 1–2180 of SEQ ID NO:5:

| | | | | |
|---|---|---|---|---|
| ATCCCTCAGC | CGCCTTTCAC | TATCTTTTTT | GCCCGAGTCA | TTGTCATGTG 50 |
| AACCTTGGCA | TGTATAATCG | GTGAATTGCG | TCGATTTTCC | TCTTATAGGT 100 |
| GGGCCAATGA | ATCCGTGTGA | TCGCGTCTGA | TTGGCTAGAG | ATATGTTTCT 150 |
| TCCTTGTTGG | ATGTATTTTC | ATACATAATC | ATATGCATAC | AAATATTTCA 200 |
| TTACACTTTA | TTAGAGGTGG | TCAGTAATAA | ACCCTATCAC | TATGTCTGGT 250 |
| GTTTCATTTT | ATTTGCTTTT | AAACGAAATT | GACTTCTGAT | TCAATATTTA 300 |
| AGGATCGCAA | TCGGCGTGCA | GTACTAATTC | TGGTTGACGG | AACTATACGT 350 |
| AAACTATTCA | GCTTCACTCT | ATTAGGCACT | ACTTGACACA | CCGGAGTACG 400 |
| TACGAATACT | CTATCAATTA | GTCTCAGTCT | AACTTGTTGA | GACATGTACT 450 |
| ATAGATTACT | ATTGTACCTT | GACTCACTGT | ATGTATCACG | TCTAATTGAA 500 |
| CTACACATAT | ATACGCGATA | TTTTTTAATA | ACATTAAAAC | CTACCTCTAT 550 |
| GTCAACAATG | GTGTACGATA | ACCACAAGTT | TAGGAGGTAA | AAAAACATTG 600 |
| CCTTACGCTG | AAGTTACGCC | TTAAAAATAA | AGAGTAAATT | TTACTTTGAC 650 |
| CACCCTTCAA | TGTTCACTTT | AGACCGGTGG | AACGCTCCAG | CCGTAATAGG 700 |
| ATTCTGCACC | TCACATGCCT | TAGCCGGATT | ATATTGCCTG | CCCACTTTCT 750 |
| CACTCATATC | TGCAAGAATG | TCTACTCGCT | AGAATTATCG | CGATAGTAGC 800 |
| TAGCATACTC | GAGGTCATTC | ATATGCTTGA | GAAGAGAGTC | GGGATAGTCC 850 |
| AAAATAAAAC | AAAGGTAAGA | TTACCTGGTC | AAAAGTGAAA | ACATCAGTTA 900 |
| AAAGGTGGTA | TAAGTAAAAT | ATCGGTAATA | AAAGGTGGCC | CAAAGTGAAA 950 |
| TTTACTCTTT | TCTACTATTA | TAAAAATTGA | GGATGTTTTG | TCGGTACTTT 1000 |
| GATACGTCAT | TTTTGTATGA | ATTGGTTTTT | AAGTTTATTC | GCGATTTTGG 1050 |
| AAATGCATAT | CTGTATTTGA | GTCGGGTTTT | AAGTTCGTTT | GCTTTTGTAA 1100 |
| ATACAGAGGG | ATTTGTATAA | GAAATATCTT | TAAAAAAACC | CATATGCTAA 1150 |
| TTTGACATAA | TTTTTGAGAA | AAATATATAT | TCAGGCGAAT | TCTCACAATG 1200 |
| AACAATAATA | AGATTAAAAT | AGCTTGCCCC | CGTTGCAGCG | ATGGGTATTT 1250 |
| TTTCTAGTAA | AATAAAAGAT | AAACTTAGAC | TCAAAACATT | TACAAAAACA 1300 |
| ACCCCTAAAG | TCCTAAAGCC | CAAAGTGCTA | TGCACGATCC | ATAGCAAGCC 1350 |
| CAGCCCAACC | CAACCCAACC | CAACCCACCC | CAGTGCAGCC | AACTGGCAAA 1400 |
| TAGTCTCCAC | ACCCCGGCAC | TATCACCGTG | AGTTGTCCGC | ACCACCGCAC 1450 |
| GTCTCGCAGC | CAAAAAAAAA | AAAAGAAAGA | AAAAAAAGAA | AAAGAAAAAA 1500 |
| CAGCAGGTGG | GTCCGGGTCG | TGGGGGCCGG | AAAAGCGAGG | AGGATCGCGA 1550 |
| GCAGCGACGA | GGCCGGCCCT | CCCTCCGCTT | CCAAAGAAAC | GCCCCCCATC 1600 |
| GCCACTATAT | ACATACCCCC | CCCTCTCCTC | CCATCCCCCC | AACCCTACCA 1650 |
| CCACCACCAC | CACCACCTCC | TCCCCCCTCG | CTGCCGGACG | ACGAGCTCCT 1700 |
| CCCCCCTCCC | CCTCCGCCGC | CGCCGGTAAC | CACCCCGCGT | CCCTCTCCTC 1750 |
| TTTCTTTCTC | CGTTTTTTTT | TTCCGTCTCG | TCTCGATCTT | TGGCCTTGGT 1800 |
| AGTTTGGGGG | CGAGAGGCGG | CTTCGTCGCC | CAGATCGGTG | CGCGGGAGGG 1850 |
| GCGGGATCTC | GCGGCTGGGT | CTCGGCGTGC | GGCCGGATCC | TCGCGGGGAA 1900 |
| TGGGGCTCTC | GGATGTAGAT | CTGATCCGCC | GTTGTTGGGG | GAGATGATGG 1950 |
| GGCGTTTAAA | ATTTCGCCAT | GCTAAACAAG | ATCAGGAAGA | GGGGAAAAGG 2000 |
| GCACTATGGT | TTATATTTTT | ATATATTTCT | GCTGCTGCTC | GTCAGGCTTA 2050 |
| GATGTGCTAG | ATCTTTCTTT | CTTCTTTTTG | TGGGTAGAAT | TTGAATCCCT 2100 |
| CAGCATTGTT | CATCGGTAGT | TTTTCTTTTC | ATGATTTGTG | ACAAATGCAG 2150 |
| CCTCGTGCGG | AGCTTTTTTG | TAGGTAGAAG | ATGGCTGACG | CCGAGGATA 2199 |

The efficiency of the promoter appears to lie within nucleotides 811 to 2202 of SEQ ID NO:4, that is in the fragment having a nucleotide sequence as shown in nucleotides 1–1373 of SEQ ID NO:6:

| | | | | |
|---|---|---|---|---|
| CTCGAGGTCA | TTCATATGCT | TGAGAAGAGA | GTCGGGATAG | TCCAAAATAA | 50 |
| AACAAAGGTA | AGATTACCTG | GTCAAAAGTG | AAAACATCAG | TTAAAAGGTG | 100 |
| GTATAAGTAA | AATATCGGTA | ATAAAAGGTG | GCCCAAAGTG | AAATTTACTC | 150 |
| TTTTCTACTA | TTATAAAAAT | TGAGGATGTT | TTGTCGGTAC | TTTGATACGT | 200 |
| CATTTTTGTA | TGAATTGGTT | TTTAAGTTTA | TTCGCGATTT | TGGAAATGCA | 250 |
| TATCTGTATT | TGAGTCGGGT | TTTAAGTTCG | TTTGCTTTTG | TAAATACAGA | 300 |
| GGGATTTGTA | TAAGAAATAT | CTTTAAAAAA | ACCCATATGC | TAATTTGACA | 350 |
| TAATTTTTGA | GAAAAATATA | TATTCAGGCG | AATTCTCACA | ATGAACAATA | 400 |
| ATAAGATTAA | AATAGCTTGC | CCCCGTTGCA | GCGATGGGTA | TTTTTTCTAG | 450 |
| TAAAATAAAA | GATAAACTTA | GACTCAAAAC | ATTTACAAAA | ACAACCCCTA | 500 |
| AAGTCCTAAA | GCCCAAAGTG | CTATGCACGA | TCCATAGCAA | GCCCAGCCCA | 550 |
| ACCCAACCCA | ACCCAACCCA | CCCCAGTGCA | GCCAACTGGC | AAATAGTCTC | 600 |
| CACACCCCGG | CACTATCACC | GTGAGTTGTC | CGCACCACCG | CACGTCTCGC | 650 |
| AGCCAAAAAA | AAAAAAAGAA | AGAAAAAAAA | GAAAAAGAAA | AAACAGCAGG | 700 |
| TGGGTCCGGG | TCGTGGGGGC | CGGAAAAGCG | AGGAGGATCG | CGAGCAGCGA | 750 |
| CGAGGCCGGC | CCTCCCTCCG | CTTCCAAAGA | AACGCCCCCC | ATCGCCACTA | 800 |
| TATACATACC | CCCCCCTCTC | CTCCCATCCC | CCCAACCCTA | CCACCACCAC | 850 |
| CACCACCACC | TCCTCCCCCC | TCGCTGCCGG | ACGACGAGCT | CCTCCCCCCT | 900 |
| CCCCCTCCGC | CGCCGCCGGT | AACCACCCCG | CGTCCCTCTC | CTCTTTCTTT | 950 |
| CTCCGTTTTT | TTTTTCCGTC | TCGTCTCGAT | CTTTGGCCTT | GGTAGTTTGG | 1000 |
| GGGCGAGAGG | CGGCTTCGTC | GCCCAGATCG | GTGCGCGGGA | GGGGCGGGAT | 1050 |
| CTCGCGGCTG | GGTCTCGGCG | TGCGGCCGGA | TCCTCGCGGG | GAATGGGGCT | 1100 |
| CTCGGATGTA | GATCTGATCC | GCCGTTGTTG | GGGGAGATGA | TGGGGCGTTT | 1150 |
| AAAATTTCGC | CATGCTAAAC | AAGATCAGGA | AGAGGGGAAA | AGGGCACTAT | 1200 |
| GGTTTATATT | TTTATATATT | TCTGCTGCTG | CTCGTCAGGC | TTAGATGTGC | 1250 |
| TAGATCTTTC | TTTCTTCTTT | TTGTGGGTAG | AATTTGAATC | CCTCAGCATT | 1300 |
| GTTCATCGGT | AGTTTTTCTT | TTCATGATTT | GTGACAAATG | CAGCCTCGTG | 1350 |
| CGGAGCTTTT | TTGTAGGTAG | AAGATGGCTG | ACGCCGAGGA | TA | 1392 | nucleotides 811 to 816 and 2199 to 2204 of SEQ ID NO:4 are the Xho1 and EcoRV enzyme sites, respectively; 2051 to 3600 nucleotides encompass the coding region DNA sequence for the rice actin gene RAc1; and 1650 to 3974 nucleotides is the RAc1 genomic clone for pRAc1.

To determine if any of the previously isolated plant actin genes also contain 5'-intron-like sequences, the region 5' of their respective translation initiation codons was compared to that of RAc1, and those animal actin genes known to contain such 5°-introns were also compared. This analysis revealed that the soybean (*Glycine max*) actin genes SAc3 and SAc1, the *Arabidopdid thaliana* actin gene AAc1, the potato (*Solanum tuberosum*) actin processed pseudogene PAc-psi, and the maize (*Zea mays*) actin gene MAc1 have regions upstream of their translation initiation codons which bear sequence similarity to the 3'-splice site junction regions of the 5'-introns of the rice actin gene RAc1, a *Xenopus borealis* cytoplasmic actin gene and the *Drosophilia melanogaster* cytoplasmic actin gene DmA2. These previously confirmed, and putative intron splice sites are all found within 7 to 11 bp upstream of their respective translation initiation codons. Although the short region of untranslated exons they would encode are all AT-rich, they do not as a group suggest any strong consensus sequence. However, these sequences may serve a similar function in the different actin genes.

The complete structural analysis of the RAc1 gene described above has therefore led to the identification and localization of a 5' noncoding exon, separated by a 5'-intron from the first coding exon, in the RAc1 genomic sequence. It has been reported that a 5'-intron in the maize Adh1 gene is essential for the efficient expression of foreign genes from the maize Adh1 promoter [Callis et al., 'Introns increase gene expression in cultured maize cells. Genes & Development, 1:1183 (1987)]. In order to investigate the effect of the RAc1 5'-intron on gene expression, a number of GUS fusion plasmids containing RAc1 intron deletion plasmids were constructed. These constructs the successive removal of those intron sequence elements previously determined as being important for efficient intron splicing, such as the mRNA branch point and 3'-donor splice sites. The results of transient assays of GUS activity in rice protoplasts transformed with the various deletion constructs suggest that the 5'-intron of RAc1 is essential for efficient gene expression from the RAc1 promoter. Test results also suggest that the intron-mediated stimulation of gene expression is not a function of the intron sequence per se but is associated, in part, with an in vivo requirement for efficient intron splicing.

This analysis and following discussion of the identification and localization of the 5' noncoding exon in the RAc1 genomic sequence can be more easily understood with references to the following examples:

EXAMPLE II

Genomic Clone Characterization:

A genomic restriction map of the 15.1 kb insert from lambda-RAc1 was prepared by analyzing all possible single and double digests with the enzymes BamHI, EcoRI, HindIII and SalI. A 5.3 kb HindIII-HindIII restriction fragment from the lambda-RAc1 clone was subcloned into pBS-KS to generate the plasmid pRAc15'.H3. A restriction map of pRAc15'.H3 was prepared by analyzing all possible single and double digests with the enzymes BamHI, BglII, EcoRI, EcoRV, HincII, HindIII, KpnI, PstI SmaI, SphI, XbaI and Xho1. Restriction digestion, plasmid ligation, transformation of *E. coli* DH5-alpha competent cells and isolation of plasmid DNA were done following standard procedures.

Figure 2A:
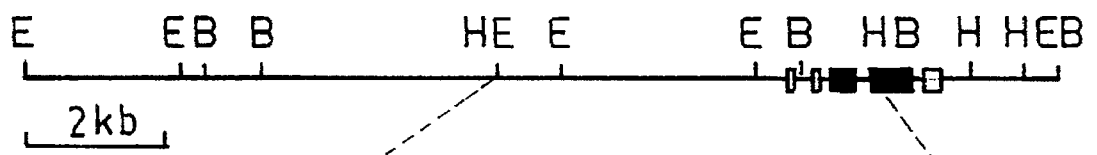
FIG. 2a is a restriction map of the 15.1 Kb lambda-RAc1 insert, according to the 2resent invention.
Figure 2A:
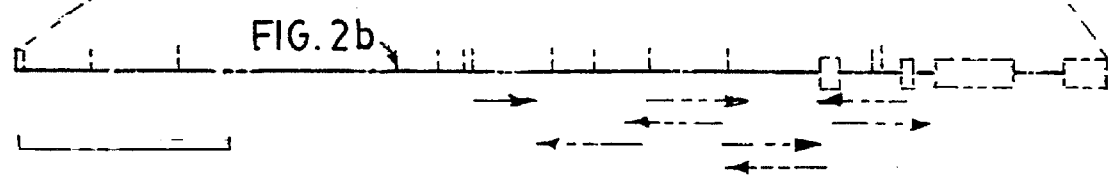
Figure 2B:
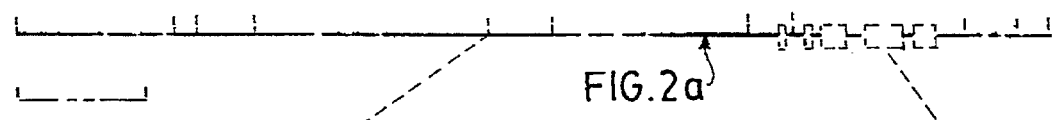
FIG. 2b is a restriction map of the pRAc 15'.H3 insert according to the present invention.
Figure 2B:
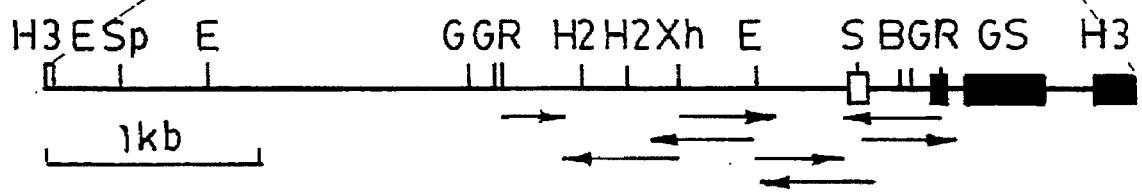
Figure 3A:
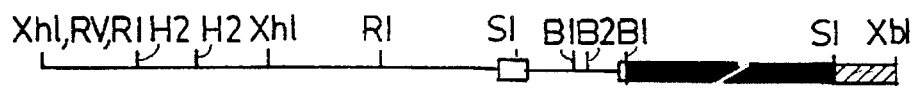
FIG. 3 depicts maps of constructs according to the present invention.
Figure 3B:
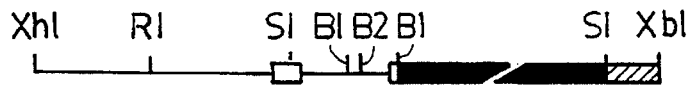
Figure 3C:
Figure 3D:
Figure 3E:
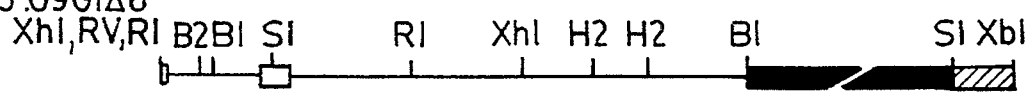
Figure 3F:
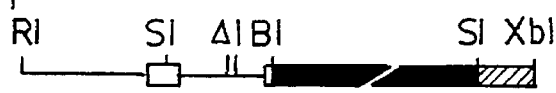
Figure 3G:
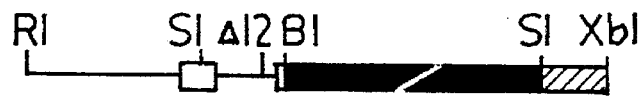
Figure 3H:
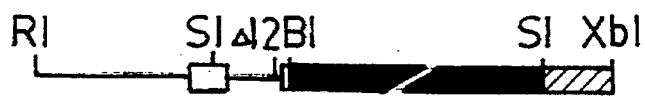
Figure 3I:
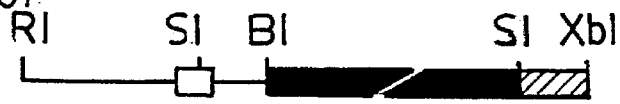
Figure 3J:
Figure 3K:
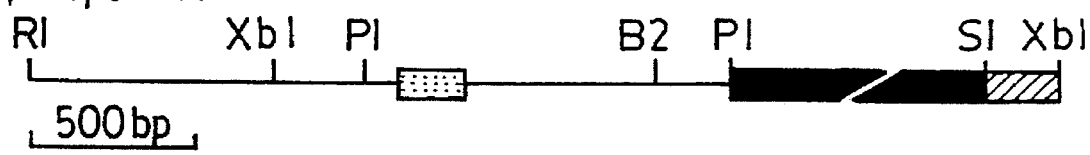

A 2.1 kb EcoRV-EcoRV region within the pRAc15'.H3 insert was further subcloned into pBS-KS and its DNA sequence determined according to the sequencing strategy outlined in FIG. 2B. Double stranded DNA sequencing reactions were run using the dideoxy chain termination method following T7 polymerase™ protocol. Analysis of DNA sequence data were performed using the Microgenie™ computer program.

EXAMPLE III

Construction of Plasmids:

The 2.1 kb EcoRV-EcoRV fragment from pRAc15'.H3 was subcloned into the SmaI site of pBluescript-KS, in both orientations, to produce the plasmids pRAc15'.21V and pRAc15'.21V^r. A promoterless β-glucuronidase (GUS) gene, containing the 3° noncoding region of the nopaline synthase (NOS) gene, was excised by BamHI-XbaI digestion of pEXAG3 and cloned between the BamHI and XbaI sites of pRAc15'.21V and pRAc15'.21V^r to produce the plasmids pRAc15'.21VG and pRAc15'.21V^rG. Deletion of the 0.8 kb XhoI-XhoI and 1.2 kb EcoRI-EcoRI fragments from pRAc 15'.21VG generated the plasmids pRAc15'.13XG and pRAc15'.09RG respectively. Introduction of the 1.2 kb EcoRI-EcoRI fragment into the EcoRI site of pRAc15'.09RG, in the reverse orientation, produced the plasmid pRAc15'.21VR^rG. The plasmid pRAc15'.09RGIDS⁻ was produced by deletion of a 0.17 kb BamHI-BamHI fragment from pRAc15'.09RG.

The plasmids pRAc15'.09RGIΔ8, pRAc15'.09RGIΔ1 and pRAc15'.09RG1Δ12 were generated by cleavage of pRAc15'.09RG at its BglII site followed by exonuclease III deletion and S1 nuclease treatment to remove different amounts of the RAc1 first intron. To construct the plasmid pRAc15'.09RGI⁻ the 0.9 kb EcoRI-EcoRV fragment from pRAc15'.H3, containing the first intron of the rice RAc1 gene, was cloned between the EcoRI and EcoRV sites of pBR322 to produce the plasmid pBRAc15'.09R. The 0.4 kb SstI-EcoRV fragment from pBRAc15'.09R, containing the RAc1 intron, was excised and replaced with the intronless 0.1 kb SstI-EcoRV fragment from the insert of an RAc1 cDNA clone, pcRAc1.3, to produce the plasmid pBRAc15'.09RI⁻. The intronless 0.6 kb EcoRV fragment from pBRAc15'.09RI⁻ was excised and cloned between the EcoRI and SmaI sites of pBS-KS to yield the plasmid pRAc15'.09RI⁻. Cloning of the GUS-NOS containing BamHI-XbaI fragment from pEXAG3 between the BamHI and XbaI site of pRAc15.09RI⁻ produced the plasmid pRAc15'.09RGI⁻. The nature of this RAc1 promoter-GUS fusion was confirmed by sequencing double-stranded DNA.

EXAMPLE IV

Culture, transformation and visualization of GUS activity in rice cell suspension cultures and protoplasts:

Cell suspension cultures were generated from calli, initiated from scutella of mature rice (*Oryza sativa* L. v Lemont) seeds, and cultured in liquid R2 media containing 3% (w/v) sucrose, 2 mg/ml 2,4-dichlorophenoxyacetic acid and 2 mg/l vitamin B-5. All cell suspensions were subcultured weekly and incubated in the dark at 26° C. Cell suspensions were filtered through a 700 µm mesh prior to particle gun bombardment with 1.2 µm diameter tungsten particles mixed with a solution containing 10 µg of plasmid DNA. GUS activity in intact cells and developing calli was determined by the appearance of blue spots two and ten days after bombardment with plasmid DNA following the GUS assay procedure of Jefferson et al.

Protoplasts were isolated from rice (*Oryza sativa* L. v Nipponvare) cell suspension cultures and resuspended in MaMg medium to a final density of $10^6$ protoplasts/ml. For transformation, 1 ml of protoplast suspension was incubated with 10 µg of circular plasmid DNA, 50 µg/ml of calf thymus carrier DNA and an equal volume of 30% polyethylene glycol 4000. The mixture was incubated for 30 minutes, diluted with CPW13 medium, washed a further 3 times in CPW13 media, with centrifugation between each wash, before being resuspended in simplified KPR liquid media to a final density of $10^6$ protoplasts/ml. 0.1 ml aliquots of this final suspension were incubated by thin layer culture in 96-well plates prior to subsequent assays for GUS activity.

EXAMPLE V

Analysis of GUS activity in transformed protoplasts:

To monitor the temporal pattern of GUS expression for each plasmid in transformed rice protoplasts, two wells from each thin layer culture were assayed 1, 3, 5, 10, 20 and 30 days after transformation. Cells were incubated with 5-bromo-4-chloro-3-indolyly glucuronide in a standard assay procedure for 48 hours before visualizing GUS activity.

For the quantitative analysis of GUS activity, cells were collected 20 days after transformation by low speed centrifugation in a bench top microcentrifuge. Total soluble protein was isolated in a GUS extraction buffer. Protein extracts were incubated with 1 mM methylumbelliferyl-β-D-glucuronide (MUG) in a standard assay at 37° C. for 3 to 6 hours. The liberation of 4-methylumbelliferone (MU) was followed by measuring fluorescence with excitation at 365 nm and emission at 455 nm in a spectrofluorometer. Protein concentrations of plant extracts were determined by the dye-binding method of Bradford. Statistical analysis of the quantitative GUS activity results were done using a paired t-test.

To begin the analysis of the rice RAc1 regulatory regions, restriction mapping of a lambda-EMBL4 phage clone, lambda-RAc1, which had previously been shown to contain the rice RAc1 gene was carried out. The resulting restriction map of the 15.1 kb lambda-RAc1 insert is shown in FIG. 2A. This figure also indicates the position of the RAc1 coding and noncoding exons, as previously determined. To isolate and characterize the 5'-flanking sequence of the rice RAc1 gene, a 5.3 kb HincII fragment from the lambda-RAc1 insert, spanning a region from 3.9 kb upstream of the RAc1 coding sequence to a point within its third coding exon, was isolated and cloned into the HindIII site of the plasmid pBluescript-KS to produce the plasmid pRAc15'.H3. A restriction map of the pRAc15'.H3 insert is shown in FIG. 2B. Restriction maps of the lambda-RAc1 (A) and pRAc15'.H3 (b) inserts were determined by single and double restriction enzyme digestion, as detailed in the methods. The enzyme sites are abbreviated as follows: BamHI B; BglII, G; EcoRI, E; EcoRV, R; HincII, H2; HindIII, H3; SphI, Sp; SstI S; XhoI, Xh. The position of the 5.3 kb Hind III fragment within the lambda-RAc1 insert is indicated by dashed lines between (A) and (B). Noncoding and coding portions of RAc1 exons are depicted by open and filled boxes respectively. The strategy used to sequence the 2.1 kb EcoRV fragment within the pRAc15'.H3 insert is indicated by horizontal arrows. The length of the horizontal arrows are indicative of the size of the sequence obtained.

The restriction map of the pRAc15'.H3 insert shown in FIG. 2B also indicates the strategy used to sequence an EcoRV fragment which covers a region 2.1 kb upstream of the translation initiation codon of the RAc1 gene. This sequence is as follows SEQ ID NO:7:

```
801  AGCTAGCATA CTCGAGGTCA TTCATATGCT TGAGAAGAGA           XhoI
     GTCGGGATAG TCCAAAATAA AACAAAGGTA AGATTACCTG
```

-continued

```
 881   GTCAAAAGTG AAAACATCAG TTAAAAGGTG GTATAAGTAA
       AATATCGGTA ATAAAAGGTG GCCCAAAGTG AAATTTACTC
 961   TTTTCTACTA TTATAAAAAT TGAGGATGTT TTGTCGGTAC
       TTTGATACGT CATTTTTGTA TGAATTGGTT TTTAAGTTTA                    i
1041   TTCGCGATTT TGGAAATGCA TATCTGTATT TGAGTCGGGT                    i
       TTTAAGTTCG TTTGCTTTTG TAAATACAGA GGGATTTGTA
1121   TAAGAAATAT CTTTAAAAAA ACCCATATGC TAATTTGACA
       TAATTTTTGA GAAAAATATA TATTCAGGCG AATTCTCACA                    EcoRI
1201   ATGAACAATA ATAAGATTAA AATAGCTTGC CCCCGTTGCA
       GCGATGGGTA TTTTTTCTAG TAAAATAAAA GATAAACTTA
1281   GACTCAAAAC ATTTACAAAA ACAACCCCTA AAGTCCTAAA                    ii
       GCCCAAAGTG CTATGCACGA TCCATAGCAA GCCCAGCCCA                    iii
1361   ACCCAACCCA ACCCAACCCA CCCCAGTGCA GCCAACTGGC
       AAATAGTCTC ACACCCCGG CACTATCACC GTGAGTGTC
1441   CGCACCACCG CACGTCTCGC AGCCAAAAAA AAAAAAAGAA                    iv
       AGAAAAAAAA GAAAAAGAAA AAACAGCAGG TGGGTCCGGG
1521   TCGTGGGGGC CGGAAAAGCG AGGAGGATCG CGAGCAGCGA
       CGAGGCCGGC CCTCCCTCCG CTTCCAAAGA AACGCCCCC
1601   ATCGCCACTA TATACATACC CCCCCCTCTC CTCCCATCCC                    v
       CCCAACCCTA CCACCACCAC CACCACCACC TCCTCCCCCC                    vi
1681   TCGCTGCCGG ACGACGAGCT CCTCCCCCCT CCCCCTCCGC                    Sst I
       CGCCGCCGGT AACCACCCCG CGTCCCTCTC CTCTTTCTTT
1761   CTCCGTTTTT TTTTTCCGTC TCGTCTCGAT CTTTGGCCTT
       GGTAGTTTGG GGGCGAGAGG CGGCTTCGTC GCCCAGATCG
1841   GTGCGCGGGA GGGGCGGGAT CTCGCGGCTG GGTCTCGGCG
       TGCGGCCGGA TCCTCGCGGG GAATGGGGCT CTCGGATGTA                    Bam HI
1921   GATCTGATCC GCCGTTGTTG GGGGAGATGA TGGGGCGTTT                    Bgl II
       AAAATTTCGC CATGCTAAAC AAGATCAGGA AGAGGGGAAA
2001   AGGGCACTAT GGTTTATATT TTTATATATT TCTGCTGCTG
       CTCGTCAGGC TTAGATGTGC TAGATCTTTC TTTCTTCTTT...                BGl II
2081   TTGTGGGTAG AATTTGAATC CCTCAGCATT GTTCATCGGT
       AGTTTTTCTT TTCATGATTT GTGACAAATG CAGCCTCGTG
2161   CGGAGCTTTT TTGTAGGTAG AAG ATG GCT GAC GCC GAG
       GAT ATC...EcoRV
```

In the above, the amino acids expressed by the last 7 triplets of the nucleic acid sequence are SEQ ID NO:8:

Met Ala Asp Ala Glu Asp Ile

In this nucleotide sequence, nucleotides are numbered with the A of the RAc1 transcription initiation site designated in bold. Restriction sites used in the subsequent construction of the various RAc1-GUS fusion plasmids and structural regions described in detail are underlined and named or designated by lower case Roman numerals and noted at the right margin of the sequence table. Upper case capital letters represent 5'-flanking sequences, upper case italic letters represent exon sequences and upper case capital letters between the two sets of exon sequences represent the intron sequence. The codons of the RAc1 first coding exon have their translation product indicated below them.

A number of potential regulatory sequences were identified in the 5'-flanking region of RAc1 gene. A 12 bp direct repeat, SEQ ID NO:9: GGTTTTAAGTT (region i), is located between bases 1024 to 1035 and 1075 to 1086. A tandem (imperfect) direct repeat of 16 bp, AA(G/C)CCC(T) AAAGT(G/C)CTA (region ii), is located between bases 1301 and 1333. 20 bp downstream of this tandem direct repeat are eight tandem copies of an imperfectly repeating pentamer with the consensus sequence CCCAA (region iii). Finally, between bases 1465 and 1505, there is a purine rich sequence where 35 out of 40 bases are "A"s (region iv).

Downstream of these putative regulatory regions a number of sequences have been identified which have previously been implicated in the control of gene expression. Between bases 1609 and 1617 there is a putative TATA box (region v). The sequence and position of the putative RAc1 TATA box are in agreement with that previously determined for a number of other plant genes, and the sequence around the transcription initiation site: SEQ ID NO:10: CCTACCA is similar to the consensus sequence for transcription initiation previously determined for a number of animal YAYY and plant YYYAYYA genes (Y=pyrimidine). The noncoding exon located 3' of the TATA box is GC rich (77.5%) and consists of a number of tandemly repeated (A/T)CC triplets (region vi).

The 5'-intron of the rice RAc1 gene is 313 bp long. Its 5'-acceptor splice site [(G/G)TA], and 3'-donor splice site [SEQ ID NO:11: TTTTTTGTA(G/G)], follow the consensus sequence previously determined for a number of plant genes. A putative branch point site for mRNA splicing between bases 2008 and 2012 (region vii) was identified whose sequence, SEQ ID NO:12: GTGAC, and distance from the 3'-donor splice site bears similarity to the location and consensus sequence for animal mRNA branch point splice sites, YTRAC.

Four RAc1-GUS fusion plasmids were constructed to determine the minimum amount of RAc1 5'-flanking sequence required for maximal β-glucuronidase (GUS) gene expression; these are shown in FIG. 3. The plasmid pRAc15'.21VG has the 2.1 kb EcoRV restriction fragment from pRAc15'.H3 fused to the GUS coding region and 3'-noncoding transcript terminator region of the nopaline synthase (NOS) gene. This plasmid encodes a transcript containing two in frame translation start codons, one each from the RAc1 and GUS genes, adding 15 amino acids to the N-terminal end of the wild type GUS protein. The plasmids pRAc15'.13XG and pRAc15'.09RG were created by the deletion of 0.8 and 1.2 kb of sequence, respectively, from the 5' end of pRAc15'.21VG. The plasmid pRAc15'.21VR'G has the 5' 1.2 kb EcoRI fragment cloned in the opposite orientation to that in pRAc15'.21VG.

A number of plasmids were also constructed to investigate the importance of the RAc1 5'-intron on RAc1-promoter-mediated gene expression. The plasmid pRAc15'.09RGIA8 contains a deletion of 9 bp around the BglII site of the RAc1 5'-intron. The plasmid pRAc15'.09RG1Δ1 contains a deletion of 133 bp between bases 1868 and 2001 of the sequence depicted above, reducing the distance between the 5' acceptor and mRNA branch point from its 5'-intron. The plasmid pRAc15'.09RGIΔ12 has a deletion of 157 bp between bases 1968 and 2125, removing the putative mRNA branch point from its 5'-intron. The plasmid pRAc15'.09RGIDS⁻ was created by excision of a 170 bp BamHI fragment from pRAc15'.09RG, removing the putative mRNA branch point and 3'-donor splicing sites from the RAc1 5'-intron. The plasmid pRAc15'.09RGI⁻ is identical to pRAc15'.09RG except that it lacks the entire RAc1 5'-intron.

The plasmid pRAc15'.21V'G contains the 2.1 kb EcoRV fragment from pRAc15'.H3 cloned in the opposite orientation to that in pRAc15'.21VG. It was postulated that the RAc1 5'-region would not show bidirectional promoter activity because the 5'-most 1.2 kb EcoRV-EcoRI restriction fragment in pRAc15.21VG did not show any binding when used as a probe in Northern hybridization against total RNA from 7 day old rice shoots. As a positive control, the plasmid pAI$_1$ GusN was used. This plasmid contains the promoter, first exon and first intron of the maize Adh1 gene fused to a GUS coding sequence with the 3' noncoding region of the NOS gene.

More specifically, individual maps of constructs containing various portions of the 5'-flanking and 5'-transcribed sequence of the rice RAc1 gene fused, in frame, to a sequence containing the GUS coding region and 3' NOS transcription terminator are shown in FIG. 3. Open boxes represent noncoding exons of the RAc1 gene, filled boxed represent the GUS coding region (not to scale) and striped boxes represent the NOS terminator sequence. The stippled box in the construct pAI$_1$ GusN represents the first exon of the maize Adh1 gene. The 'Δ' symbol indicates the deletion point in the various RAc1 first intron deletion constructs. The indicated restriction enzyme sites are abbreviated as follows: BamHI B1; BglII, B2; EcoRI, R1; EcoRV, RV; HincII, H2; HindIII, H3; SstI, S1; Xho1, Xh1; Xba1, Xb1.

To assay GUS expression from the various RAc1-GUS fusion plasmids, rice suspension culture cells were transformed by the biolistic method [see Wang, Y. C. et al., Transient expression of foreign genes in rice, wheat, and soybean cells following particle bombardment. Plant Mol. Biol. 11:433 (1987); and Cai, J. et al., Transformation of rice and maize using the biolistic process. UCLA Symposia on Plant Gene Transfer (1989)], and assayed for high level GUS activity by visual inspection 10 days after transformation according to Jefferson [GUS fusions: β-glucuronidase as a sensitive and versatile gene fusion marker in higher plants. EMBO J. 6:3901 (1987)].

Results of these various assays are tabulated below:

TABLE 1

| Names | Protoplasts: | | Cell |
|---|---|---|---|
| | mean specific Activity nmol/min/μg | mean GUS Expression % | Suspension Visible GUS Activity |
| pRAc15'.21VG | 211.4[1] | 8.4 | + |
| pRAc15'.13XG | 195.0[1] | 7.9 | + |
| pRAc15'.09RG | 94.2[2] | 5.7 | + |
| pRAc15'.21VR'G | 92.5[2] | 6.1 | + |
| pRAc15'.09RGIΔ8 | 95.4[2] | 2.8 | N.A. |
| pRAc15'.09RGIΔ1 | 53.4[3] | 1.4 | N.A. |
| pRAc15'.09RGIΔ12 | 17.0[4] | 0.2 | N.A. |
| pRAc15'.09RGIDS⁻ | 8.8[5] | 0.2 | N.A. |

TABLE 1-continued

| Names | Protoplasts: | | Cell |
|---|---|---|---|
| | mean specific Activity nmol/min/μg | mean GUS Expression % | Suspension Visible GUS Activity |
| pRAc15'.09RGI⁻ | 4.7[5] | 0.2 | — |
| pRAc15'.21V'G | 0.7[5] | 0.0 | — |
| Untransformed | 0.0[5] | 0.0 | — |
| pAI$_1$GusN | 31.9[6] | 4.2 | + |

N.A. = not assayed

The results of the rapid assay are shown in the third column of Table 1. Suspension cultures transformed with the plasmids pRAc15'.21VG, pRAc15'.13XG, pRAc15'.09RG, pRAc15'.21VR'G and pAI$_1$GusN were all positive for GUS activity while untransformed cultures or those transformed with pRAc15'.09RGI⁻ or pRAc15.21V'G displayed no visible GUS expression.

Table I also shows the results of a determination of GUS expression efficiencies, defined as the percent of intact cells displaying visible GUS activity 10 days after PEG-mediated transformation of rice protoplasts with the RAc1-GUS fusion constructs. The plasmids pRAc15'.21VG and pRAc15'.13XG displayed the highest GUS expression efficiencies at 8.4 and 7.9% respectively. The plasmids pRAc15'.09RG and pRAc15'.21VR'G showed GUS expression efficiencies of 5.7 and 6.1%, respectively. All four of the aforementioned plasmids displayed significantly higher GUS expression efficiencies than was found for pAI$_1$ GusN. Removal of RAc1 5'-intron sequences resulted in a significant reduction in the number of cells displaying visible GUS activity, relative to pRAc15'.09RG, which contains the intact RAc1 5'-intron. For plasmids pRAc15'.09RGIΔ8 (2.8%) and pRAc15'.09RGIΔ1 (1.4%), the longer the sequence deleted between the 5'-acceptor and the putative mRNA branch point splice sites, the lower the GUS expression efficiency. Removal of the branch point for mRNA splicing in the plasmid pRAc15'.09RGIΔ12 and the additional removal of the 3'-donor splice site in the plasmid pRAc15'.09RGIDS⁻ led to GUS expression efficiencies which, at 0.2%, represents less than 4% of that determined for the plasmid pRAc15'.09RG. Untransformed protoplasts or protoplasts transformed with either pRAc15'.21V'G or the intronless plasmid pRAc15'.09RGI⁻ gave no blue cells.

To determine the quantitative differences in GUS expression from the various RAc1-GUS fusion plasmids, the constructs were introduced into rice protoplasts by PEG-mediated transformation, and GUS specific activity was assayed 20 days after the transformation procedure. The results of this quantitative analysis of GUS expression are presented in the first column of Table I.

The highest GUS specific activities were recorded for the plasmids pRAc15'.21VG and pRAc15'.13XG, which have the longest RAc1 upstream regions. The plasmid pAI$_1$GusN, which has the GUS gene expressed under control of the maize Adh1 promoter, displayed less than 17% of the GUS specific activity shown by pRAc15'.21VG and pRAc15'.13XG. The plasmids pRAc15'.09RG, with a truncated RAc1 5'-region, and pRAc15'.21VR'G, with an inverted RAc1 5'-region, were found to have GUS specific activities around 48% of that for pRAc15'.21VG. There was no statistically significant difference (mean specific activity with identical superscripted numbers are not statistically different from each other), in specific activity between these two constructs, suggesting that the inversion of the RAc1

5'-end did not influence GUS expression from the truncated RAc15'.09RG construct.

The effects of the various RAc1 intron deletions could be seen when their GUS specific activities were compared to that of their progenitor plasmid, pRAc15'.09RG. The small 9 bp deletion in the RAc1 5'-intron of plasmid pRAc15'.09RGIΔ8 had no effect on the quantitative level of GUS activity. The plasmid pRAc15'.09RGIΔ1, containing a deletion of 133 bp between the 5'-acceptor splice site and the putative mRNA branch point splice site, displayed a GUS specific activity that was less than 57% of that observed for pRAc15'.09RG. The plasmid pRAc15'.09RGIΔ12, which had the putative mRNA branch point site removed, showed a further decrease in GUS specific activity of 17% of that observed for pRAc15'.09RG. The plasmid pRAc15'.09RGIDS⁻, which lacks the putative mRNA splicing branch site and 3'-splicing donor site of the RAc1 5'-intron, and pRAc15'.09RGI⁻, which lacks the entire RAc1 5'-intron, displayed no significant GUS specific activities over that observed for untransformed samples. However, it was noted in Table I that while blue cells, indicative of GUS expression, were never observed in untransformed rice protoplasts or protoplasts transformed with the intronless plasmid pRAc15'.09RGI⁻, GUS expression was able to be visualized in those rice protoplasts transformed with the plasmid pRAc15'.09RGIDS⁻.

As a first step towards an understanding of the regulation of rice actin gene expression, the present invention has described the isolation and characterization of the 5'-regions of the rice RAc1 gene. Within the 5'-flanking sequence, the occurrence of a long poly(dA) stretch located between bases 1465 and 1505 which appears to play a role in the constitutive activation of RAc1 gene expression was found. Based upon chemical analysis, it has been suggested that a minimal affinity for histone cores and nucleosome formation is provided by homogeneous tracts of purines located on one strand of the double helix. Poly(dA) regions within recombinant DNA molecules can prevent nucleosome formation in vitro, and it has also been found that naturally occurring poly(dA) tracts act as 5'-promoter elements for the constitutive expression of different yeast genes. It is believed that poly(dA) stretches may change the chromatin structure, enabling general transcription factors to access the DNA template and activate constitutive transcription in the absence of more specific transcription factors.

The sequence of RAc1 untranslated mRNA 5'-region is unusually GC rich, with an AT content of only 26.5%. In a survey of 79 plant genes it was found that their mRNA 5'-sequences were extremely AT rich, with 71 of the genes surveyed having an AT content greater than 51% and only one of the genes surveyed having an AT content of less than 44%. In the ribosomal-scanning model of translation initiation it is proposed that the AT richness of the mRNA 5'-sequence leads to the formation of relatively labile secondary structures which facilitate the movement of the ribosomal subunits towards the translation initiation codon. The significance of the GC rich RAc1 m RNA 5'-sequence, with respect to transcript stability and translation efficiency, remains to be investigated.

The construction of a number of RAc1-GUS fusion constructs has provided the determination that the plasmid pRAc15'.13XG, containing 0.83 kb of 5'-flanking sequence, the noncoding exon and 5'-intron of the RAc1 gene, has the minimal amount of RAc1 sequence necessary for maximal GUS expression in transient assays of transformed rice protoplasts; the additional 0.8 kb of RAc1 5'-sequence present in the pRAc15'.13VG did not significantly increase GUS expression above that of the plasmid pRAc15'.13XG. It was also found in the present invention that the RAc1 5'-flanking sequence was more active than the maize Adh1 5'-flanking region in stimulating GUS expression in transformed rice protoplasts. Deletion of a 0.4 kb region from the 5'-end of the pRAc15'.13XG insert resulted in a 52% reduction in GUS activity. However, no statistically significant difference in GUS specific activities was detected between the plasmids pRAc15'.09RG, with the 0.4 kb region deleted, and pRAc15'.13.09RG, with the 0.4 kb deleted, and pRAc15'.21VR′G, with the 0.4 kb region present but inverted and displaced 0.8 kb further upstream. This suggests that the sequence element(s) in the 5'-end of the pRAc15'.13XG insert that are responsible for high level GUS expression do not display any position/orientation-independent, enhancer-like activity. In most cases the differences in GUS specific activities detected between the RAc1-GUS fusion constructs could be directly correlated with their differential GUS expression efficiencies. This suggests that there is a threshold to the visualization of GUS expression. Protoplasts transformed with the various RAc1-GUS fusion constructs are presumed to display a position-effect-dependent distribution of GUS specific activities, the mean of which is a function of their particular RAc1 promoter. Therefore those protoplast populations transformed with the most active RAc1 promoter-GUS fusion constructs will display the greatest number of visually detectable blue cells and the highest GUS expression efficiencies.

By constructing RAc1-intron-deletion-GUS plasmids, it was able to be shown that GUS expression in transformed rice protoplasts was dependent on the presence of an intact RAc1 5'-intron. Deletion of the RAc1 intron reduced GUS specific activity to levels that were not significantly greater than that of untransformed protoplasts. In transient assays of transformed maize protoplasts a maize Adh1-S gene lacking the nine Adh1-S introns was expressed at levels 50- to 100-times lower than that of the intact gene. The reintroduction of the 5'-intron of the Adh1-S gene was enough to restore the level of expression to that observed for the intact gene, although this effect was only observed if the first intron was reinserted in a 5'-position; it is believed that this was a result of increases in the amount of mature, cytoplasmic mRNA and not a result of increased transcript stability in the nucleus or increased translation efficiency in the cytoplasm.

The increase in expression resulting from the presence of RAc1 5'-intron is not believed to be caused by the presence of some enhancer-like cis acting sequence within the intron. No sequences within the RAc1 intron were found which bore any homology to either an enhancer-like sequence from the first intron of the human cytoplasmic actin gene, or to any sequences within the maize Adh1 5'-intron. Nor is it believed that the RAc1 first intron codes for any functionally active transcript or protein product. Previous Northern blot hybridization with a double stranded probe that spans the RAc1 first intron failed to show any binding to total RNA from seven day old rice shoots, other than to the 1.7 kb RAc1 transcript itself. Finally, the RAc1 5'-intron contains no open reading frames of any significant length. One conclusion of the present invention suggests that the primary effect of RAc1 first intron is associated with an in vivo requirement for efficient splicing.

The small deletion in the RAc1 intron in the plasmid pRAc15'.09RGIΔ8 caused no significant reduction in GUS specific activity relative to that of pRAc15'.09RG. However, a significant difference was observed between the GUS specific activities of the plasmids pRAc15'.09RG and pRAc15'.09RGIΔ1. The 133 bp deletion in the plasmid pRAc15'.09RGIΔ1, while not removing any of the sequences previously implicated in intron splicing, did cause a reduction in the distance between the 5'-acceptor and putative mRNA branch point splice sites with an associated 44% reduction in GUS specific activity. Large reductions in splicing efficiency occur in vivo and in vitro when the distance between the 5'-acceptor and branch point splice sites is reduced; this requirement for a minimal distance between the 5'-acceptor and branch point splice sites probably reflects a requirement for multiple splicing factors to interact with specific intron regions, these regions being presumably removed in the construction of pRAc15'.09RGIΔ1. The in vivo requirement for efficient intron splicing was further supported by the observation that a deletion which removed the putative 5'-intron mRNA branch point splice site in the construction of pRAc15'.09RGIΔ12, or removed both the branch point and 3'-donor splice sites in the construction of pRAc15'.09RIDS⁻ led to GUS specific activities which were 18% and 9% of that observed for pRAc15'.09RG. Deletion of the normal branch point and 3'-donor splice sites of animal genes does not abolish splicing but rather leads to the use of cryptic branch point and 3'-donor splice sites, with associated reductions in splicing efficiency and gene expression; this may be occurring in rice protoplasts transformed with the plasmids pRAc15'.09RGIΔ12 and pRAc15'.09RGIDS⁻, leading to reduced but still detectable GUS expression.

The results of the present invention clearly demonstrate that the RAc1 5'-flanking sequence between 0 and 2070 nucleotides and more particularly between 800 and 2070 nucleotides in the genomic sequence contains an efficient promoter for rice transformation. Furthermore, the expression of a foreign gene in transformed plant cells can be dependent upon, but not necessarily an absolute function of, the presence of an intact 5'-intron sequence. It appears that a functional requirement for the presence of the 5'-intron may be correlated with the conservation of the 5' noncoding exon during this rice actin gene's structural evolution. In addition the results of the present invention indicate that the maize 5'-intron is located between the first and second coding exons of the Adh1 gene, while the rice 5'-intron is located between a 5' noncoding exon and the first coding exon of the RAc1 gene, suggesting that there may be a common positional component to the intron mediated stimulation of gene expression observed for the maize and rice 5'-intron.

In summary, the preceding description of the present invention clearly demonstrates that a 2.1 kbp 5' of the Act1 gene's translation initiation codon, containing 1.3 kb of 5' untranscribed sequence, the 5' transcribed but untranslated exon, 5'-intron and part of the first coding exon of the rice Act1 gene, is capable of conferring high level expression of foreign gene in transformed rice material. Thus this region can be used to activate the constitutive expression of foreign genes in transgenic plants of rice and other agronomically important plants; the 5'-intron of the rice Act1 gene can stimulate the expression of a foreign gene in transformed rice material [thus this (and the other introns of the rice Act1 gene) will be able to increase the expression of foreign genes in transformed plants of rice (and other agronomically important plants) when cloned into such genes]; and although no specific function for the 3'-end of the rice Act1 gene in the regulation of foreign gene expression in rice has been demonstrated. It appears from the present invention that the 3'-end of the rice Act1 gene should also stimulate the expression of such foreign genes in transformed plants of rice and other agronomically important crops.

In the transient gene expression studies described above, we have identified important features for obtaining high levels of Act1-mediated gene expression, and have found that optimal levels of gene expression can be obtained from plasmids, that were so constructed that Gus transcripts contained both Act1 intron 1 and, surrounding the first ATG codon, a sequence context that favors translation initiation. Based upon these findings, a set of Act1 5'-based vectors for use in monocot transformation studies has been developed. Both translational and transcriptional fusion expression vectors have been constructed, as shown in the following Table 2 depicting polylinker sites of the Act1-based expression vectors.

TABLE 2

| Plasmids | Vect.[a] | Size[b] | 5' P[c] | 5' Polylinker restriction sites[d] | Polylinker restriction sites[d] | 3' P[c] |
|---|---|---|---|---|---|---|
| pAct1-B | BS | 5.2 | RP | Kpni, Apal, Xhol, Accl, Hincil, Sall, Clal, HindIII, EcoRV, EcoR1, Pstl | BamHI, Spel, Xbal, Notl, Eagl, BstXI, SstII, SstI | T7 |
| pAct1-C | BS | 5.2 | T7 | SstI, SstII, BstXI, Eagl, Notl, Xbal, Spel, BamHI | Pstl, EcoR1, EcoRv, HindIII, Clal, Sall, Hincll, Accl, Xhol, Apal, Kpnl | RP |
| pCOR101 | BS | 5.2 | RP | Kpnl, Apal, Xhol, Accl, Hincll, Sall, Clal, HindIII, EcoRV | Accl, Ncol, EcoRV, EcoR1, Pstl, Smal, BamHI, Spel, Xbal, Notl, Eagl, BstXI, SstII, SstI | T7 |
| pCor102 | BS | 5.2 | T7 | SstI, SstII, BstXI, Eagl, Notl, Xbal, Spel, BamHI, Smal, Pstl, EcoR1, EcoRV | Accl, Ncol, EcoRV, HindIII, Clal, Sall, Hincll, Accl, Xhol, Apal, Kpnl | RP |
| pCOR106 | 5Zf | 5.2 | T7 | Apal, Xhol, Accl, Hincll, Sall, Clal, EcoRV, HindIII | Accl, Ncol, SstII, EcoRV, Spel, Notl, Pstl, . . . Accl, Hincll, Sall, SstI, BstXI | SP6 |
| pCOR109 | 5Zf | 5.2 | T7 | Apal, AatII, Sphl, Eagl, Notl, Xbal, Spel, BamHI, Smal, Pstl, EcoR1, EcoRV | Accl, Ncol, SstII, EcoRV, Spel, Notl, Pstl, Accl, Hincll, Sall, SstI, BstXI | SP6 |
| pCOR103 | BS | 4.4 | RP | Kpnl, Apal, Xhol | Accl, Ncol, BamHI, Spel, Xbal, Notl, Eagl, BstXI, SstII, SstI | T7 |
| pCOR104 | BS | 4.4 | RP | Kpnl, Apal, Xhol | Accl, Ncol, EcoRV, EcoR1, Pstl, Smal, BamHI, Spel, Xbal, Notl, Eagl, BstXI, SstII, SstI | T7 |
| pCOR107 | 5Zf | 4.4 | T7 | Apal, Xhol | Accl, Ncol, SstII, EcoRV, Spel, Notl, Pstl, Accl, Hincll, Sall, SstI, BstXI | SP6 |
| pCOR108 | BS | 4.4 | T7 | SstI, SstII, BstXI, Eagl, Notl, Xbal, Xhol | Accl, Ncol, EcoRV, HindIII, Clal, Sall, Hincll, Accl, Xhol, Apal, Kpnl | RP |
| pCOR114 | BS | 4.4 | T7 | SstI, SstII, BstXI, Clal, Accl, Hincll Sall, Xhol | Accl, Ncol, SstII, EcoRV, Spel, Notl, Pstl, Apal, Kpnl | RP |
| pCOR112 | BS | 4.4 | RP | Kpnl, Apal, Xhol | Accl, Ncol, SstII, EcoRV, EcoR1, Pstl, Smal, | T7 |

TABLE 2-continued

| Plasmids | Vect.[a] | Size[b] | 5' P[c] | 5' Polylinker restriction sites[d] | Polylinker restriction sites[d] | 3' P[c] |
|---|---|---|---|---|---|---|
| PCOR115 | 5Zf | 4.4 | T7 | ApaI, AatII, SphI, EagI, XbaI, XhoI | BamHI, SpeI, XbaI, NotI, EagI, SstII, BstXI, SstI AccI, NcoI, SstII, EcoRV, SpeI, NotI, PstI, AccI HincII, SalI, SstI, BstXI | SP6 |
| pCOR116 | 5Zf | 4.4 | SP6 | BstXI, SstI, AccI, SalI, PstI, NotI | AccI, NcoI, SstII, EcoRV, SpeI, XbaI, EagI, SphI, AatII, ApaI | T7 |
| pCOR105 | BS | 4.4 | RP | KpnI, ApaI, XhoI | AccI, EcoRV, EcoRI, PstI, SmaI, BamHI, SpeI, XbaI, NotI, EagI, BstXI, SstII, SstI | T7 |
| pCOR113 | BS | 4.4 | RP | KpnI, ApaI, XhoI | AccI, HindIII, EcoRV, EcoRI, PstI, SmaI, BamHI, SpeI, XbaI, NotI, EagI, BstXI, SstII, SstI | T7 |
| PCOR117 | 5Zf | 4.4 | SP6 | BstXI, SstI, AccI, SalI, PstI, NotI | AccI, SstII, EcoRV, SpeI, XbaI, EagI, SphI, AatII, ApaI | T7 |

[a]Plasmid used in vector construction: BS is BluescriptII-KS (2.96 kb); 5Zf is pGem-5Zf(+)(3.00 kb).
[b]Size of the vector/Act1 5' region in kilobases.
[c]Sequencing primer binding site at the 5' and 3' ends of the Act1 region: RP is M13 reverse primer; T7 is T7 17-mer primer; SP6 is SP6 17-mer primer
[d]Polylinker restriction sites and the 5' and 3' ends of the Act1 region; unique restriction sites in the expression vector are in italic letters In Table 2, pCOR105, pCOR113 and pCOR117 are transcriptional fusion vectors, whereas all other vectors are translational fusion expression vectors. These expression vectors contain a number of unique polylinker sites located both upstream (5' polylinker sites) and downstream (3' polylinker sites) of their respective Act1 5' regions in order to simplify subsequent cloning procedures. The nucleotide sequence at the junction of the Act1 transcribed region and polylinker region in each expression vector, and their relationship to the Act1-Gus fusion plasmids used in the transient gene expression assays are presented in the following Table 3:

TABLE 3

```
pAct1-F    GTAGAAG ATG GCTGACGCCGAGGATGGGGGATCCCACTAGTTCTAGAGCGGTCCCTT ATGTTACGTCCTGTAGAA
                                     RV/Sma   BamHI  SmaI                     SEQ ID NO: 13:
                                                           NotI       BstXI
                                                                SpeI  XbaI  EagI       SstII pAct1-B    GTAGAAG ATG GCTGACGCCGAGGATGGGGGATCCACTAGTTCTAGAGCGGCCGCCACCGCGTGGAGCTC      SEQ ID NO: 14:
                                      RV/Sma   BamHI  SmaI
                                                     SpeI XbaI EagI        SstII pAct1-C    GTAGAAG ATG GCTGACGCCGAGGATGGGGCTGCAGGAATTCGATATCAAGCTTATCGATACCGTCGACCTCGAGGGGGGCCCGTACC
                                                                                              SEQ ID NO: 15:
                         PstI  EcoRI EcoRV HindIII ClaI SalI XhoII ApaI KpnI
                                                                 HincII
                                                                 AccI pAct1-F4   AccI   NcoI    SEQ ID NO: 16:
           GTAGACC ATGGTCGTCCTGTAGAA
           AccI   NcoI pAct1-F2   GTAGACC ATG GCTGACGCCGAGGATGGGGGATCCCCGGGTGTCAGTCCCTT ATGTTACGTCCTGTAGAA       SEQ ID NO: 17:
           AccI   NcoI                 RV/Sma  BamHI  SmaI
                                                                     NotI       BstXI
                                                            SpeI XbaI EagI        SstII pCOR103    GTAGACC ATG GCTGACGCCGAGGATATCGAATTCCTGCAGCCCGGGGATCCACTAGTTCTAGAGCGGCCGCCACCGCGTGGAGCTC     SEQ ID NO: 18:
           AccI   NcoI                  EcoRV  EcoRI  PstI SmaI BamHI SpeI XbaI EagI        SstII
                                                                                    NotI       BstXI pCOR101    GTAGACC ATG GCTGACGCCGAGGATATCGAATTCCTGCAGCCCGGGGATCCACTAGTTCTAGAGCCCGCCACCGCGTGGAGCTC       SEQ ID NO: 19:
pCOR104    AccI   NcoI                  EcoRV  EcoRI  PstI SmaI BamHI SpeI XbaI EagI        SatII
                                                                                                SstI pCOR102    GTAGACC ATG GCTGACGCCGAGGATATCAAGCTTATCGATACCGTCGACCTCGAGGGGGGGCCCGTACC                      SEQ ID NO: 20:
pCOR108    AccI   NcoI                  EcoRV  HindIII ClaI SalI XhoI ApaI KpnI
                                                                                    NotI       BstXI pCOR112    GTAGACC ATG GCCGCGGGATATCGAATTCCTGCAGCCCGGGGATCCACTAGTTCTAGAGCGGCCGCCACCGCGTGGAGCTC          SEQ ID NO: 21:
           AccI   NcoI       SstII      EcoRV  EcoRI  PstI SmaI BamHI SpeI XbaI EagI        SatII
                                                                                                SstI
                                                                                    NotI       BstXI pCOR116    GTAGACC ATG GCCGCGGGATATCACTAGTTCTAGAGCGGCCGCATGGCAGCGTCGGGCC                                SEQ ID NO: 22:
           AccI   NcoI       SstII      EcoRV  SpeI XbaI EagI        SphI AatII ApaI pCOR106... GTAGACC ATG GCCGCGGGATATCACTAGTGCGGCCGCCTGCAGGTCGACCATATGGGAGAGCTCCAACGCGTTGG               SEQ ID NO: 23:
pCOR107    AccI   NcoI       SstII      EcoRV  SpeI   EcoRV   NotI    PstI SalI                  SstII       BstXI
pCOR109                                                                                                  HincII
pCOR115                                                                                                  AccI pACT1-F5   Acc/Sma           SEQ ID NO: 24:
           GTAGGGGTGGTCAGTCCCTT ATGTTACGTCCTAGGA
           AccI pCOR105    GTAGACCCCTGACGCCGAGGATATCGAATTCCTGCAGCCCGGGGATCCACTAGTTCTAGAGCGGCCGCCACCGCGTGGAGCTC         SEQ ID NO: 25:
           AccI                         EcoRV  ECORI  PstI SmaI BamHI SpeI XbaI EagI        SatII
                                                                                                SstI
                                                                                    NotI       BstXI
```

TABLE 3-continued

|  | | |
|---|---|---|
| pCOR113 | GTAGACGATCCGCTTGATATCGAATTCCTGCAGCCCGGGGATCCACTAGTTCTAGAGCGGCCGCCACCGCGTGGAGCTC<br>AccI  HindIII  EcoRV  EcoRI  PstI  SmaI  BamHI  SpeI  XbaI  NotI  EagI  BstXI  SstII  SstI | SEQ ID NO: 26: |
| pCOR117 | GTAGACCGCGGGATATCACTAGTTCTAGAGGCCGGAGCATGCGACGTCGGGCCC<br>AccI  SstII  EcoRV  SpeI  XbaI  EagI  SphI  AatI  ApaI | |

While we have illustrated and described the preferred embodiment of our invention, it is to be understood that this invention is capable of variation and modification and we therefore do not wish or intend ourselves to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and a process of making and using it in such clear, full, concise and exact terms so as to enable any person skilled in the art to which it pertains, or with which it is mostly nearly connected, to make and use the same;

We claim:

1. An isolated nucleic acid molecule encoding a promoter region from rice actin 1 gene.

2. A fragment of the nucleic acid molecule of claim 1 wherein said fragment has promoter activity in monocotyledonous plants.

3. An isolated nucleic acid molecule encoding a promoter region from rice actin 1 gene wherein said nucleic acid molecule has a nucleotide sequence as shown in nucleotides 1–2180 of SEQ ID NO:5.

4. A fragment of the nucleic acid molecule of claim 3, wherein said fragment consists essentially of nucleotides 1–1373 of SEQ ID NO:6.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AAGCGGCCTC TACTACGC    18

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GAAGCATTTC CTGTGCACAA T    21

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CTTCTACCGG CGGCGGC    17

( 2 ) INFORMATION FOR SEQ ID NO:4:

( i ) SEQUENCE CHARACTERISTICS:
        ( A ) LENGTH: 5643 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GATATCCCTC AGCCGCCTTT CACTATCTTT TTTGCCCGAG TCATTGTCAT GTGAACCTTG    60

GCATGTATAA TCGGTGAATT GCGTCGATTT TCCTCTTATA GGTGGGCCAA TGAATCCGTG    120

```
TGATCGCGTC  TGATTGGCTA  GAGATATGTT  TCTTCCTTGT  TGGATGTATT  TTCATACATA     180
ATCATATGCA  TACAAATATT  TCATTACACT  TTATTAGAGG  TGGTCAGTAA  TAAACCCTAT     240
CACTATGTCT  GGTGTTTCAT  TTTATTTGCT  TTTAAACGAA  ATTGACTTCT  GATTCAATAT     300
TTAAGGATCG  CAATCGGCGT  GCAGTACTAA  TTCTGGTTGA  CGGAACTATA  CGTAAACTAT     360
TCAGCTTCAC  TCTATTAGGC  ACTACTTGAC  ACACCGGAGT  ACGTACGAAT  ACTCTATCAA     420
TTAGTCTCAG  TCTAACTTGT  TGAGACATGT  ACTATAGATT  ACTATTGTAC  CTTGACTCAC     480
TGTATGTATC  ACGTCTAATT  GAACTACACA  TATATACGCG  ATATTTTTA   ATAACATTAA     540
AACCTACCTC  TATGTCAACA  ATGGTGTACG  ATAACCACAA  GTTAGGAGG   TAAAAAAACA     600
TTGCCTTACG  CTGAAGTTAC  GCCTTAAAAA  TAAAGAGTAA  ATTTACTTT   GACCACCCTT     660
CAATGTTCAC  TTTAGACCGG  TGGAACGCTC  CAGCCGTAAT  AGGATTCTGC  ACCTCACATG     720
CCTTAGCCGG  ATTATATTGC  CTGCCCACTT  TCTCACTCAT  ATCTGCAAGA  ATGTCTACTC     780
GCTAGAATTA  TCGCGATAGT  AGCTAGCATA  CTCGAGGTCA  TTCATATGCT  TGAGAAGAGA     840
GTCGGGATAG  TCCAAAATAA  AACAAGGTA   AGATTACCTG  GTCAAAAGTG  AAAACATCAG     900
TTAAAAGGTG  GTATAAGTAA  AATATCGGTA  ATAAAAGGTG  GCCCAAAGTG  AAATTTACTC     960
TTTTCTACTA  TTATAAAAAT  TGAGGATGTT  TTGTCGGTAC  TTTGATACGT  CATTTTTGTA    1020
TGAATTGGTT  TTTAAGTTTA  TTCGCGATTT  TGGAAATGCA  TATCTGTATT  TGAGTCGGGT    1080
TTTAAGTTCG  TTTGCTTTTG  TAAATACAGA  GGGATTTGTA  TAAGAAATAT  CTTTAAAAAA    1140
ACCCATATGC  TAATTTGACA  TAATTTTTGA  GAAAAATATA  TATTCAGGCG  AATTCTCACA    1200
ATGAACAATA  ATAAGATTAA  AATAGCTTGC  CCCGTTGCA   GCGATGGGTA  TTTTTTCTAG    1260
TAAAATAAAA  GATAAACTTA  GACTCAAAAC  ATTTACAAAA  ACAACCCCTA  AAGTCCTAAA    1320
GCCCAAAGTG  CTATGCACGA  TCCATAGCAA  GCCCAGCCCA  ACCCAACCCA  ACCCAACCCA    1380
CCCCAGTGCA  GCCAACTGGC  AAATAGTCTC  CACACCCCGG  CACTATCACC  GTGAGTTGTC    1440
CGCACCACCG  CACGTCTCGC  AGCCAAAAAA  AAAAAAGAA   AGAAAAAAAA  GAAAAGAAA     1500
AAACAGCAGG  TGGGTCCGGG  TCGTGGGGGC  CGGAAAAGCG  AGGAGGATCG  CGAGCAGCGA    1560
CGAGGCCGGC  CCTCCCTCCG  CTTCCAAAGA  AACGCCCCCC  ATCGCCACTA  TATACATACC    1620
CCCCCTCTC   CTCCCATCCC  CCAACCCTA   CCACCACCAC  CACCACCACC  TCCTCCCCCC    1680
TCGCTGCCGG  ACGACGAGCT  CCTCCCCCCT  CCCCCTCCGC  CGCCGCCGGT  AACCACCCCG    1740
CGTCCCTCTC  CTCTTTCTTT  CTCCGTTTTT  TTTTTCCGTC  TCGTCTCGAT  CTTTGGCCTT    1800
GGTAGTTTGG  GGGCGAGAGG  CGGCTTCGTC  GCCCAGATCG  GTGCGCGGGA  GGGGCGGGAT    1860
CTCGCGGCTG  GGTCTCGGCG  TGCGGCCGGA  TCCTCGCGGG  GAATGGGGCT  CTCGGATGTA    1920
GATCTGATCC  GCCGTTGTTG  GGGGAGATGA  TGGGGCGTTT  AAAATTTCGC  CATGCTAAAC    1980
AAGATCAGGA  AGAGGGGAAA  AGGGCACTAT  GGTTTATATT  TTTATATATT  TCTGCTGCTG    2040
CTCGTCAGGC  TTAGATGTGC  TAGATCTTTC  TTTCTTCTTT  TTGTGGGTAG  AATTTGAATC    2100
CCTCAGCATT  GTTCATCGGT  AGTTTTCTT   TTCATGATTT  GTGACAAATG  CAGCCTCGTG    2160
CGGAGCTTTT  TTGTAGGTAG  AAGATGGCTG  ACGCCGAGGA  TATCCAGCCC  CTCGTCTGCG    2220
ATAATGGAAC  TGGTATGGTC  AAGGTAAGCT  GTTTGGATCT  CAGGGTGGTT  TCCGTTTACC    2280
GAAATGCTGC  ATTTCTTGGT  AGCAAAACTG  AGGTGGTTTG  TGTCAGGCTG  GGTTCGCCGG    2340
AGATGATGCG  CCCAGGGCTG  TCTTCCCCAG  CATTGTCGGC  CGCCCTCGCC  ACACCGGTGT    2400
CATGGTCGGA  ATGGGCCAGA  AGGACGCCTA  CGTCGGCGAC  GAGGCGCAGT  CCAAGAGGGG    2460
TATCTTGACC  CTCAAGTACC  CCATCGAGCA  TGGTATCGTC  AGCAACTGGG  ATGATATGGA    2520
```

| | | | | | |
|---|---|---|---|---|---|
| GAAGATCTGG | CATCACACCT | TCTACAACGA | GCTCCGTGTG | GCCCCGGAGG | AGCACCCCGT | 2580 |
| CCTCCTCACC | GAGGCTCCTC | TCAACCCCAA | GGCCAATCGT | GAGAAGATGA | CCCAGATCAT | 2640 |
| GTTGAGACC | TTCAACACCC | CTGCTATGTA | CGTCGCCATC | CAGGCCGTCC | TCTCTCTGTA | 2700 |
| TGCCAGTGGT | CGTACCCAAG | GTGAGCACAT | TCGACACTGA | ACTAAAGGC | TGTGAGGATG | 2760 |
| AATTTTAATT | TTGACATTCA | CATGTAGATG | AGATTAGTT | CTGCAATCTT | CAATTGTCAT | 2820 |
| ACAGCAAGAC | TATATAATAG | CTTTCAAAAT | AAAATCATAG | GCAGTTCTCA | TAAATGGAAT | 2880 |
| CATGTTGAA | CATCCTAATT | CTGTTGGCAT | GGAGTGCTTT | GACATTTGA | AGTGTGCATC | 2940 |
| AGTGTGAATA | ACTGAATTTC | CTTTTCCCAA | GGTATTGTGT | TGGACTCTGG | TGATGGTGTC | 3000 |
| AGCCACACTG | TCCCCATCTA | TGAAGGATAT | GCTCTCCCCC | ATGCTATCCT | TCGTCTCGAC | 3060 |
| CTTGCTGGGC | GTGATCTCAC | TGATTACCTC | ATGAAGATCC | TGACGGAGCG | TGGTTACTCA | 3120 |
| TTCACCACAA | CGGCCGAGCG | GGAAATTGTG | AGGGACATGA | AGGAGAAGCT | TCCTACATC | 3180 |
| GCCCTGGACT | ATGACCAGGA | AATGGAGACT | GCCAAGACCA | GCTCCTCCGT | GGAGAAGAGC | 3240 |
| TACGAGCTTC | CTGATGGACA | GGTTATCACC | ATTGGTGCTG | AGCGTTTCCG | CTGCCCTGAG | 3300 |
| GTCCTCTTCC | AGCCTTCCTT | CATAGGAATG | GAAGCTGCGG | GTATCCATGA | GACTACATAC | 3360 |
| AACTCCATCA | TGAAGTGCGA | CGTGGATATT | AGGAAGGATC | TATATGGCAA | CATCGTTCTC | 3420 |
| AGTGGTGGTA | CCACTATGTT | CCCTGGCATT | GCTGACAGGA | TGAGCAAGGA | AGATCACTGC | 3480 |
| CTTGCTCCTA | GCAGCATGAA | GATCAAGGTG | GTCGCCCCTC | CTGAAAGGAA | GTACAGTGTC | 3540 |
| TGGATTGGAG | GATCCATCTT | GGCATCTCTC | AGCACATTCC | AGCAGGTAAA | TATACAAATG | 3600 |
| CAGCAATGTA | GTGTTGTTTA | CCTCATGAAC | TTGATCAATT | TGCTTACAAT | GTTGCTGCC | 3660 |
| GTTGCAGATG | TGGATTGCCA | AGGCTGAGTA | CGACGAGTCT | GGCCCATCCA | TTGTGCACAG | 3720 |
| GAAATGCTTC | TAATTCTTCG | GACCCAAGAA | TGCTAAGCCA | AGAGGAGCTG | TTATCGCCGT | 3780 |
| CCTCCTGCTT | GTTTCTCTCT | TTTTGTTGCT | GTTTCTTCAT | TAGCGTGGAC | AAAGTTTTCA | 3840 |
| ACCGGCCTAT | CTGTTATCAT | TTTCTTCTAT | TCAAAGACTG | TAATACCTAT | TGCTACCTGT | 3900 |
| GGTTCTCACT | TGTGATTTTG | GACACATATG | TTCGGTTTAT | TCAAATTTAA | TCAGATGCCT | 3960 |
| GATGAGGGTA | CCAGAAAAAA | TACGTGTTCT | GGTTGTTTTT | GAGTTGCGAT | TATTCTATGA | 4020 |
| AATGAATAAC | ATCGAAGTTA | TCATCCCAGT | ATTTCGCAT | GAATGTTCTT | TTCTTCTGTC | 4080 |
| TTGTGCATCA | GTGATCTAGT | GCATGGGAGT | TTGTATTGTG | ATGTTCGACA | TCACGTAACT | 4140 |
| TCCACTTTGC | CTTTGCTGTT | CGATATTTTA | ATGACATGTC | ACACACACTT | CTGCTACTTT | 4200 |
| TCTTTCTTGG | CTATTGTGCC | AGCATGATGC | AAGATGCATC | ACACGATCAG | ATATATTCTC | 4260 |
| ATCGTCAGGC | TTTCAGGCAC | AGAGCACGCT | TTGCGCTTAA | AAGTTGTACC | GCCAGTAGAC | 4320 |
| ATCCCTGTA | GAAGTGATAA | TCTTTTCACT | TTTCTTAAAG | AAATTGAGAG | GGGAAATGGA | 4380 |
| ACCATGTGGA | TCAGAGAAGC | TTTTGTTTCT | TACACAAGAA | TATTTGGTAC | AGTGGGGGTC | 4440 |
| CTATGTTCGT | GGGTTCGTGG | CTTGGCTCCC | TGTCTTCAAC | CAAGTGTTTT | CAGTTCAACA | 4500 |
| TGTTAGCGTG | TAGAAAGAGC | ACAATTCTGT | TTATCTCCAA | GGTAAAATGT | GGCATTCTGT | 4560 |
| TAAAGAACAT | GATCCTGCCA | ATTTTTAAG | TTTCAATGGA | AGAGGAATGT | AAAGCTTTCT | 4620 |
| ATGGTTTGTG | TACACAACAC | AGTGGAAGAG | GAGTGCAAGC | TTTCTATGGT | TTGTGTGCGC | 4680 |
| GTTGTGGTGC | AGCACTTCAA | TTTTGTTAGA | AATGAAAGAA | AAAAAGGAT | GATCATGCTT | 4740 |
| ATAGTAAATC | ACTCTTTTTC | CTCGCCTTCT | GTACGTTTTG | ACTTGACAAG | ATTTAAAAT | 4800 |
| CTGTACATGA | CCTTTGTTTT | AAAATTACTT | TATGTATTTC | CATCTTTCAA | GTTATGCAGA | 4860 |
| TGTCATCACA | AATTGTTACA | CCAATCACCA | GGCTGGCTGT | TTATATATTA | TCAGACCAGG | 4920 |

| | | | | | | |
|---|---|---|---|---|---|---|
| CTATATAGAG | TATACTATAC | TAACTGTTCA | TATTATCTGG | AAATCTTGCT | TGCTACTTGA | 4980 |
| GCGGGAAAAG | GGTATAGATA | TGAGGTTAAG | GAACGAAGCG | GCAGCAAATC | GAGGCTCTCT | 5040 |
| CTGAAATCAT | TTTACATCTA | CAAAAGCACA | TTTAACCTTT | TCTAGAACAC | ATATGTTACT | 5100 |
| TAGAAGCAGG | AAGTTCATGC | AAAATTTCAT | CGACAAGATA | ACCAGGGCGG | CACTGGAAGA | 5160 |
| GTTATCTTTT | ACCTCAATCT | GTATACACTC | AAAGTTACTC | GGATTGTACA | TTGGCTAAAA | 5220 |
| GTTTCCCTGT | TTCATTTGAA | CCACCTCAGC | AAAAGCAACC | TGAAGAGTTT | GTTGTGCAAA | 5280 |
| GGTAAAAACC | TTCCCCCAGA | CTTTGATCCT | TCCCTTGCAT | ATCTAAGGGC | ATCACGGTGA | 5340 |
| GGTCACTGTA | CCGCAAGCAT | TAGTCCAACA | CAAAGCCATT | CTTTGCTTCT | TTTGTCCACC | 5400 |
| GTTCAATAT | GTATACATCT | GGTATGGTGC | GTACATCAAG | GGCCAAGAAT | ACTCTTAGTA | 5460 |
| TATGCCGGCA | CAAGCTACCA | CAACTCTCAA | ACTTGCAGCA | GCTGCACTTA | GCTATATTGC | 5520 |
| CAGAAGTATC | ATACCTGACT | CTGCATGTGG | CTTCAGTATG | GTCCTTTGTG | ACACTATACA | 5580 |
| CAGCAATCAA | CCCATCATTG | TCAAGACTAG | AGATATATAA | TAGCCTAAAG | ATCCAATGAA | 5640 |
| TCC | | | | | | 5643 |

(2) INFORMATION FOR SEQ ID NO:5:

(i) SEQUENCE CHARACTERISTICS:
        (A) LENGTH: 2199 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

| | | | | | | |
|---|---|---|---|---|---|---|
| ATCCCTCAGC | CGCCTTTCAC | TATCTTTTTT | GCCCGAGTCA | TTGTCATGTG | AACCTTGGCA | 60 |
| TGTATAATCG | GTGAATTGCG | TCGATTTCC | TCTTATAGGT | GGGCCAATGA | ATCCGTGTGA | 120 |
| TCGCGTCTGA | TTGGCTAGAG | ATATGTTTCT | TCCTTGTTGG | ATGTATTTTC | ATACATAATC | 180 |
| ATATGCATAC | AAATATTTCA | TTACACTTTA | TTAGAGGTGG | TCAGTAATAA | ACCCTATCAC | 240 |
| TATGTCTGGT | GTTTCATTTT | ATTTGCTTTT | AAACGAAATT | GACTTCTGAT | TCAATATTTA | 300 |
| AGGATCGCAA | TCGGCGTGCA | GTACTAATTC | TGGTTGACGG | AACTATACGT | AAACTATTCA | 360 |
| GCTTCACTCT | ATTAGGCACT | ACTTGACACA | CCGGAGTACG | TACGAATACT | CTATCAATTA | 420 |
| GTCTCAGTCT | AACTTGTTGA | GACATGTACT | ATAGATTACT | ATTGTACCTT | GACTCACTGT | 480 |
| ATGTATCACG | TCTAATTGAA | CTACACATAT | ATACGCGATA | TTTTTTAATA | ACATTAAAAC | 540 |
| CTACCTCTAT | GTCAACAATG | GTGTACGATA | ACCACAAGTT | TAGGAGGTAA | AAAAACATTG | 600 |
| CCTTACGCTG | AAGTTACGCC | TTAAAATAA | AGAGTAAATT | TTACTTTGAC | CACCCTTCAA | 660 |
| TGTTCACTTT | AGACCGGTGG | AACGCTCCAG | CCGTAATAGG | ATTCTGCACC | TCACATGCCT | 720 |
| TAGCCGGATT | ATATTGCCTG | CCCACTTTCT | CACTCATATC | TGCAAGAATG | TCTACTCGCT | 780 |
| AGAATTATCG | CGATAGTAGC | TAGCATACTC | GAGGTCATTC | ATATGCTTGA | GAAGAGAGTC | 840 |
| GGGATAGTCC | AAAATAAAAC | AAAGGTAAGA | TTACCTGGTC | AAAAGTGAAA | ACATCAGTTA | 900 |
| AAAGGTGGTA | TAAGTAAAAT | ATCGGTAATA | AAAGGTGGCC | CAAAGTGAAA | TTACTCTTT | 960 |
| TCTACTATTA | TAAAAATTGA | GGATGTTTTG | TCGGTACTTT | GATACGTCAT | TTTTGTATGA | 1020 |
| ATTGGTTTTT | AAGTTTATTC | GCGATTTGG | AAATGCATAT | CTGTATTTGA | GTCGGGTTTT | 1080 |
| AAGTTCGTTT | GCTTTTGTAA | ATACAGAGGG | ATTTGTATAA | GAAATATCTT | TAAAAAAACC | 1140 |
| CATATGCTAA | TTTGACATAA | TTTTTGAGAA | AAATATATAT | TCAGGCGAAT | TCTCACAATG | 1200 |
| AACAATAATA | AGATTAAAAT | AGCTTGCCCC | CGTTGCAGCG | ATGGGTATTT | TTTCTAGTAA | 1260 |

-continued

| | | | | | |
|---|---|---|---|---|---|
| AATAAAAGAT | AAACTTAGAC | TCAAAACATT | TACAAAAACA | ACCCCTAAAG | TCCTAAAGCC | 1320
| CAAAGTGCTA | TGCACGATCC | ATAGCAAGCC | CAGCCCAACC | CAACCCAACC | CAACCCACCC | 1380
| CAGTGCAGCC | AACTGGCAAA | TAGTCTCCAC | ACCCCGGCAC | TATCACCGTG | AGTTGTCCGC | 1440
| ACCACCGCAC | GTCTCGCAGC | CAAAAAAAAA | AAAGAAAGA | AAAAAAGAA | AAAGAAAAA | 1500
| CAGCAGGTGG | GTCCGGGTCG | TGGGGGCCGG | AAAAGCGAGG | AGGATCGCGA | GCAGCGACGA | 1560
| GGCCGGCCCT | CCCTCCGCTT | CCAAAGAAAC | GCCCCCATC | GCCACTATAT | ACATACCCCC | 1620
| CCCTCTCCTC | CCATCCCCCC | AACCCTACCA | CCACCACCAC | CACCACCTCC | TCCCCCTCG | 1680
| CTGCCGGACG | ACGAGCTCCT | CCCCCCTCCC | CCTCCGCCGC | CGCCGGTAAC | CACCCCGCGT | 1740
| CCCTCTCCTC | TTTCTTTCTC | CGTTTTTTTT | TTCCGTCTCG | TCTCGATCTT | TGGCCTTGGT | 1800
| AGTTTGGGGG | CGAGAGGCGG | CTTCGTCGCC | CAGATCGGTG | CGCGGGAGGG | GCGGGATCTC | 1860
| GCGGCTGGGT | CTCGGCGTGC | GGCCGGATCC | TCGCGGGAA | TGGGGCTCTC | GGATGTAGAT | 1920
| CTGATCCGCC | GTTGTTGGGG | GAGATGATGG | GGCGTTTAAA | ATTTCGCCAT | GCTAAACAAG | 1980
| ATCAGGAAGA | GGGGAAAAGG | GCACTATGGT | TTATATTTTT | ATATATTTCT | GCTGCTGCTC | 2040
| GTCAGGCTTA | GATGTGCTAG | ATCTTTCTTT | CTTCTTTTTG | TGGGTAGAAT | TTGAATCCCT | 2100
| CAGCATTGTT | CATCGGTAGT | TTTTCTTTTC | ATGATTTGTG | ACAAATGCAG | CCTCGTGCGG | 2160
| AGCTTTTTTG | TAGGTAGAAG | ATGGCTGACG | CCGAGGATA | | | 2199

( 2 ) INFORMATION FOR SEQ ID NO:6:

( i ) SEQUENCE CHARACTERISTICS:
        ( A ) LENGTH: 1392 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| CTCGAGGTCA | TTCATATGCT | TGAGAAGAGA | GTCGGGATAG | TCCAAAATAA | AACAAAGGTA | 60
| AGATTACCTG | GTCAAAAGTG | AAAACATCAG | TTAAAGGTG | GTATAAGTAA | AATATCGGTA | 120
| ATAAAAGGTG | GCCCAAAGTG | AAATTTACTC | TTTTCTACTA | TTATAAAAAT | TGAGGATGTT | 180
| TTGTCGGTAC | TTTGATACGT | CATTTTTGTA | TGAATTGGTT | TTTAAGTTTA | TTCGCGATTT | 240
| TGGAAATGCA | TATCTGTATT | TGAGTCGGGT | TTTAAGTTCG | TTTGCTTTTG | TAAATACAGA | 300
| GGGATTTGTA | TAAGAAATAT | CTTTAAAAAA | ACCCATATGC | TAATTTGACA | TAATTTTTGA | 360
| GAAAAATATA | TATTCAGGCG | AATTCTCACA | ATGAACAATA | ATAAGATTAA | AATAGCTTGC | 420
| CCCCGTTGCA | GCGATGGGTA | TTTTTTCTAG | TAAAATAAAA | GATAAACTTA | GACTCAAAAC | 480
| ATTTACAAAA | ACAACCCCTA | AAGTCCTAAA | GCCCAAAGTG | CTATGCACGA | TCCATAGCAA | 540
| GCCCAGCCCA | ACCCAACCCA | ACCCAACCCA | CCCCAGTGCA | GCCAACTGGC | AAATAGTCTC | 600
| CACACCCCGG | CACTATCACC | GTGAGTTGTC | CGCACCACCG | CACGTCTCGC | AGCCAAAAAA | 660
| AAAAAAAGAA | AGAAAAAAAA | GAAAAGAAA | AACAGCAGG | TGGGTCCGGG | TCGTGGGGGC | 720
| CGGAAAAGCG | AGGAGGATCG | CGAGCAGCGA | CGAGGCCGGC | CCTCCCTCCG | CTTCCAAAGA | 780
| AACGCCCCCC | ATCGCCACTA | TATACATACC | CCCCCTCTC | CTCCATCCC | CCAACCCTA | 840
| CCACCACCAC | CACCACCACC | TCCTCCCCCC | TCGCTGCCGG | ACGACGAGCT | CCTCCCCCCT | 900
| CCCCCTCCGC | CGCCGCCGGT | AACCACCCCG | CGTCCCTCTC | CTCTTTCTTT | CTCCGTTTTT | 960
| TTTTTCCGTC | TCGTCTCGAT | CTTTGGCCTT | GGTAGTTTGG | GGGCGAGAGG | CGGCTTCGTC | 1020

-continued

| | | | | | |
|---|---|---|---|---|---|
| GCCCAGATCG | GTGCGCGGGA | GGGGCGGGAT | CTCGCGGCTG | GGTCTCGGCG | TGCGGCCGGA | 1080 |
| TCCTCGCGGG | GAATGGGGCT | CTCGGATGTA | GATCTGATCC | GCCGTTGTTG | GGGGAGATGA | 1140 |
| TGGGGCGTTT | AAAATTTCGC | CATGCTAAAC | AAGATCAGGA | AGAGGGGAAA | AGGGCACTAT | 1200 |
| GGTTTATATT | TTTATATATT | TCTGCTGCTG | CTCGTCAGGC | TTAGATGTGC | TAGATCTTTC | 1260 |
| TTTCTTCTTT | TTGTGGGTAG | AATTTGAATC | CCTCAGCATT | GTTCATCGGT | AGTTTTTCTT | 1320 |
| TTCATGATTT | GTGACAAATG | CAGCCTCGTG | CGGAGCTTTT | TTGTAGGTAG | AAGATGGCTG | 1380 |
| ACGCCGAGGA | TA | | | | | 1392 |

( 2 ) INFORMATION FOR SEQ ID NO:7:

( i ) SEQUENCE CHARACTERISTICS:
        ( A ) LENGTH: 1404 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| AGCTAGCATA | CTCGAGGTCA | TTCATATGCT | TGAGAAGAGA | GTCGGGATAG | TCCAAAATAA | 60 |
| AACAAAGGTA | AGATTACCTG | GTCAAAAGTG | AAAACATCAG | TTAAAAGGTG | GTATAAGTAA | 120 |
| AATATCGGTA | ATAAAAGGTG | GCCCAAAGTG | AAATTTACTC | TTTTCTACTA | TTATAAAAAT | 180 |
| TGAGGATGTT | TTGTCGGTAC | TTTGATACGT | CATTTTGTA | TGAATTGGTT | TTTAAGTTTA | 240 |
| TTCGCGATTT | TGGAAATGCA | TATCTGTATT | TGAGTCGGGT | TTTAAGTTCG | TTTGCTTTTG | 300 |
| TAAATACAGA | GGGATTTGTA | TAAGAAATAT | CTTTAAAAAA | ACCCATATGC | TAATTTGACA | 360 |
| TAATTTTTGA | GAAAAATATA | TATTCAGGCG | AATTCTCACA | ATGAACAATA | ATAAGATTAA | 420 |
| AATAGCTTGC | CCCCGTTGCA | GCGATGGGTA | TTTTTTCTAG | TAAAATAAAA | GATAAACTTA | 480 |
| GACTCAAAAC | ATTTACAAAA | ACAACCCCTA | AAGTCCTAAA | GCCCAAAGTG | CTATGCACGA | 540 |
| TCCATAGCAA | GCCCAGCCCA | ACCCAACCCA | ACCCAACCCA | CCCCAGTGCA | GCCAACTGGC | 600 |
| AAATAGTCTC | CACACCCCGG | CACTATCACC | GTGAGTTGTC | CGCACCACCG | CACGTCTCGC | 660 |
| AGCCAAAAAA | AAAAAAAGAA | AGAAAAAAA | GAAAAGAAA | AAACAGCAGG | TGGGTCCGGG | 720 |
| TCGTGGGGC | CGGAAAAGCG | AGGAGGATCG | CGAGCAGCGA | CGAGGCCGGC | CCTCCCTCCG | 780 |
| CTTCCAAAGA | AACGCCCCCC | ATCGCCACTA | TATACATACC | CCCCCCTCTC | CTCCCATCCC | 840 |
| CCCAACCCTA | CCACCACCAC | CACCACCACC | TCCTCCCCCC | TCGCTGCCGG | ACGACGAGCT | 900 |
| CCTCCCCCCT | CCCCCTCCGC | CGCCGCCGGT | AACCACCCCG | CGTCCCTCTC | CTCTTTCTTT | 960 |
| CTCCGTTTTT | TTTTTCCGTC | TCGTCTCGAT | CTTTGGCCTT | GGTAGTTTGG | GGGCGAGAGG | 1020 |
| CGGCTTCGTC | GCCCAGATCG | GTGCGCGGGA | GGGGCGGGAT | CTCGCGGCTG | GGTCTCGGCG | 1080 |
| TGCGGCCGGA | TCCTCGCGGG | GAATGGGGCT | CTCGGATGTA | GATCTGATCC | GCCGTTGTTG | 1140 |
| GGGGAGATGA | TGGGGCGTTT | AAAATTTCGC | CATGCTAAAC | AAGATCAGGA | AGAGGGGAAA | 1200 |
| AGGGCACTAT | GGTTTATATT | TTTATATATT | TCTGCTGCTG | CTCGTCAGGC | TTAGATGTGC | 1260 |
| TAGATCTTTC | TTTCTTCTTT | TTGTGGGTAG | AATTTGAATC | CCTCAGCATT | GTTCATCGGT | 1320 |
| AGTTTTTCTT | TTCATGATTT | GTGACAAATG | CAGCCTCGTG | CGGAGCTTTT | TTGTAGGTAG | 1380 |
| AAGATGGCTG | ACGCCGAGGA | TATC | | | | 1404 |

( 2 ) INFORMATION FOR SEQ ID NO:8:

( i ) SEQUENCE CHARACTERISTICS:
        ( A ) LENGTH: 7 amino acids ( B ) TYPE: amino acid
            ( C ) STRANDEDNESS: Not Relevant
            ( D ) TOPOLOGY: linear ( i i ) MOLECULE TYPE: peptide ( x i ) SEQUENCE DESCRIPTION: SEQ ID NO:8:

Met Ala Asp Ala Glu Asp Ile
    1               5

( 2 ) INFORMATION FOR SEQ ID NO:9:

( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:9:

GGTTTTAAGT T                                                                                11

( 2 ) INFORMATION FOR SEQ ID NO:10:

( i ) SEQUENCE CHARACTERISTICS:
            ( A ) LENGTH: 7 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:10:

CCTACCA                                                                                      7

( 2 ) INFORMATION FOR SEQ ID NO:11:

( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:11:

TTTTTGTAG                                                                                   10

( 2 ) INFORMATION FOR SEQ ID NO:12:

( i ) SEQUENCE CHARACTERISTICS:
            ( A ) LENGTH: 5 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:12:

GTGAC                                                                                        5

( 2 ) INFORMATION FOR SEQ ID NO:13:

( i ) SEQUENCE CHARACTERISTICS:
            ( A ) LENGTH: 70 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:13:

GTAGAAGATG GCTGACGCCG AGGATGGGGG ATCCCCGGGT GGTCAGTCCC TTATGTTACG 60

TCCTGTAGAA 70

( 2 ) INFORMATION FOR SEQ ID NO:14:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GTAGAAGATG GCTGACGCCG AGGATGGGGG ATCCACTAGT TCTAGAGCGG CCGCCACCGC 60

GGTGGAGCTC 70

( 2 ) INFORMATION FOR SEQ ID NO:15:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GTAGAAGATG GCTGACGCCG AGGATGGGCT GCAGGAATTC GATATCAAGC TTATCGATAC 60

CGTCGACCTC GAGGGGGGGC CCGTACC 88

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GTAGACCATG GTCCGTCCTG TAGAA 25

( 2 ) INFORMATION FOR SEQ ID NO:17:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GTAGACCATG GCTGACGCCG AGGATGGGGG ATCCCCGGGT GGTCAGTCCC TTATGTTACG 60

TCCTGTAGAA 70

( 2 ) INFORMATION FOR SEQ ID NO:18:

( i ) SEQUENCE CHARACTERISTICS:
        ( A ) LENGTH: 70 base pairs
        ( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:18:

GTAGACCATG GCTGACGCCG AGGATGGGGG ATCCACTAGT TCTAGAGCGG CCGCCACCGC    60

GGTGGAGCTC    70

( 2 ) INFORMATION FOR SEQ ID NO:19:

( i ) SEQUENCE CHARACTERISTICS:
    ( A ) LENGTH: 88 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:19:

GTAGACCATG GCTGACGCCG AGGATATCGA ATTCCTGCAG CCCGGGGGAT CCACTAGTTC    60

TAGAGCGGCC GCCACCGCGG TGGAGCTC    88

( 2 ) INFORMATION FOR SEQ ID NO:20:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:20:

GTAGACCATG GCTGACGCCG AGGATATCAA GCTTATCGAT ACCGTCGACC TCGAGGGGGG    60

GCCCGGTACC    70

( 2 ) INFORMATION FOR SEQ ID NO:21:

( i ) SEQUENCE CHARACTERISTICS:
    ( A ) LENGTH: 83 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:21:

GTAGACCATG GCCGCGGGAT ATCGAATTCC TGCAGCCCGG GGATCCACT AGTTCTAGAG    60

CGGCCGCCAC CGCGGTGGAG CTC    83

( 2 ) INFORMATION FOR SEQ ID NO:22:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:22:

GTAGACCATG GCCGCGGGAT ATCACTAGTT CTAGAGCGGC CGGGAGCATG CGACGTCGGG    60

CCC    63

( 2 ) INFORMATION FOR SEQ ID NO:23:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

```
GTAGACCATG GCCGCGGGAT ATCACTAGTG CGGCCGCCTG CAGGTCGACC ATATGGAGA       60
GCTCCCAACG CGTTGG                                                      76
```

( 2 ) INFORMATION FOR SEQ ID NO:24:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

```
GTAGGGGTGG TCAGTCCCTT ATGTTACGTC CTGTAGGA                              38
```

( 2 ) INFORMATION FOR SEQ ID NO:25:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

```
GTAGACCCTG ACGCCGAGGA TATCGAATTC CTGCAGCCCG GGGGATCCAC TAGTTCTAGA       60
GCGGCCGCCA CCGCGGTGGA GCTC                                              84
```

( 2 ) INFORMATION FOR SEQ ID NO:26:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

```
GTAGACGATC CGCTTGATAT CGAATTCCTG CAGCCCGGGG GATCCACTAG TTCTAGAGCG       60
GCCGCCACCG CGGTGGAGCT C                                                 81
```

( 2 ) INFORMATION FOR SEQ ID NO:27:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

```
GTAGACCGCG GGATATCACT AGTTCTAGAC GGCCGGGAGC ATGCGACGTC GGGCCC           56
```